US008568792B2

(12) United States Patent
Roberts et al.

(10) Patent No.: US 8,568,792 B2
(45) Date of Patent: Oct. 29, 2013

(54) METAL COMPOUNDS, MIXED OR SULPHATED, AS PHOSPHATE BINDERS

(75) Inventors: Norman B Roberts, Liverpool (GB); Maurice Webb, Chester (GB); Benjamin J Rankin, York (GB)

(73) Assignee: Cytochroma Development Inc., Markham (CA)

( * ) Notice: Subject to any disclaimer, the term of this patent is extended or adjusted under 35 U.S.C. 154(b) by 4 days.

(21) Appl. No.: 12/828,462

(22) Filed: Jul. 1, 2010

(65) Prior Publication Data

US 2011/0014301 A1 Jan. 20, 2011

Related U.S. Application Data

(60) Division of application No. 10/615,797, filed on Jul. 10, 2003, now Pat. No. 7,799,351, which is a continuation of application No. 09/508,923, filed as application No. PCT/GB98/02834 on Sep. 18, 1998, now Pat. No. 6,926,912.

(30) Foreign Application Priority Data

Sep. 19, 1997 (GB) .................................. 9720061.2

(51) Int. Cl.
*A01N 59/16* (2006.01)
*A61K 33/26* (2006.01)

(52) U.S. Cl.
USPC ............ 424/646; 424/647; 424/648; 514/961

(58) Field of Classification Search
None
See application file for complete search history.

(56) References Cited

U.S. PATENT DOCUMENTS

| | | |
|---|---|---|
| 2,222,924 A | 11/1940 | Weiss |
| 2,812,344 A * | 11/1957 | Oroshnik ...................... 556/147 |
| 3,395,211 A | 7/1968 | Wielich |
| 3,650,704 A | 3/1972 | Kumura et al. |
| 3,743,098 A | 7/1973 | Martinez |
| 3,796,792 A | 3/1974 | Miyata et al. |
| 3,879,523 A | 4/1975 | Miyata et al. |
| 3,984,392 A | 10/1976 | van der Veen et al. |
| 4,254,099 A | 3/1981 | Asmussen et al. |
| 4,351,814 A | 9/1982 | Miyata et al. |
| 4,370,280 A | 1/1983 | Oediger et al. |
| 4,415,555 A | 11/1983 | Anabuki et al. |
| 4,458,026 A | 7/1984 | Reichle |
| 4,514,389 A | 4/1985 | Miyata |
| 4,566,986 A | 1/1986 | Waldmann |
| 4,582,705 A | 4/1986 | Primes et al. |
| 4,609,543 A | 9/1986 | Morris et al. |
| 4,629,626 A | 12/1986 | Miyata et al. |
| 4,661,330 A | 4/1987 | Chane-Ching et al. |
| 4,735,629 A | 4/1988 | Glemser et al. |
| 4,786,510 A | 11/1988 | Nakel et al. |
| 4,970,079 A | 11/1990 | Hem et al. |
| 4,994,283 A | 2/1991 | Mehansho et al. |
| 5,002,747 A | 3/1991 | Le Loarer |
| 5,085,869 A | 2/1992 | Olthoff et al. |
| 5,173,284 A | 12/1992 | Moisset et al. |
| 5,213,794 A | 5/1993 | Fritsch et al. |
| 5,246,899 A | 9/1993 | Bhattacharyya |
| 5,506,248 A | 4/1996 | Nikfar et al. |
| 5,514,281 A | 5/1996 | Boos et al. |
| 5,525,305 A | 6/1996 | Minekus et al. |
| 5,571,336 A | 11/1996 | Wurzburger et al. |
| 5,651,997 A | 7/1997 | Makino et al. |
| 5,654,011 A | 8/1997 | Jackson et al. |
| 5,656,080 A | 8/1997 | Staniforth et al. |
| 5,817,340 A | 10/1998 | Roche et al. |
| 5,846,426 A | 12/1998 | Boos et al. |
| 5,968,976 A | 10/1999 | Murrer et al. |
| 6,028,023 A | 2/2000 | Vierheilig |
| 6,039,981 A | 3/2000 | Woo et al. |
| 6,103,126 A | 8/2000 | Boos et al. |
| 6,174,442 B1 | 1/2001 | Geisser et al. |
| 6,287,596 B1 | 9/2001 | Murakami et al. |
| 6,448,323 B1 | 9/2002 | Jordan et al. |
| 6,576,665 B2 | 6/2003 | Dennett, Jr. et al. |
| 6,596,311 B1 | 7/2003 | Dobetti |
| 6,696,087 B2 | 2/2004 | Matsuda et al. |
| 6,720,005 B1 | 4/2004 | Ayres |

(Continued)

FOREIGN PATENT DOCUMENTS

| | | |
|---|---|---|
| CA | 1198674 A1 | 12/1985 |
| DE | 2061136 A1 | 7/1971 |

(Continued)

OTHER PUBLICATIONS

Hansen et al (Synthesis and characterization of pyrourite, Applied Clay Science vol. 10, 1995, pp. 5-19).*
Abramowitz M. et al., Serum Alkaline Phosphatase and Phosphate and Risk of Mortality and Hospitalization, Clin, J. Am. Soc. Nephrol, 2010 vol. 5, No. 6 p. 1064-1071.
Schwarz S. et al., Association of Disorders in Mineral Metabolism with Progression of Chronic Kidney Disease, Clin. J. Am. Soc. Nephrol., 2006, vol. 1, p. 825-831.
Naylor T.A. et al., Use of gastro-intestinal model and gastroplus for the prediction of in vivo performance, Industrial Pharmacy, Dec. 2006, issue 12, p. 9-12.
Larsson M. et al., Estimation o the bioavailability of iron and phosphorus in cereals using a dynamic in vitro gastrointestinal model, J. Sci. Food Agric, 1997, vol. 74, p. 99-106.

(Continued)

*Primary Examiner* — Alton Pryor
(74) *Attorney, Agent, or Firm* — Marshall, Gerstein & Borun LLP

(57) ABSTRACT

A mixed metal compound for pharmaceutical use is free from aluminium and has a phosphate binding capacity of at least 30%, by weight of the total weight of phosphate present, over a pH range of from 2-8. The compound is especially useful for treatment of hyperphosphataemia. The metals are preferably iron (III) and at least one of calcium, magnesium, lanthanum and cerium. A metal sulphate for pharmaceutical use is selected from at least one of calcium, lanthanum and cerium sulphate compounds and has a phosphate binding capacity of at least 30% by weight of the total phosphate present, over a pH range from 2-8.

22 Claims, 10 Drawing Sheets

(56) References Cited

U.S. PATENT DOCUMENTS

Figure 1:
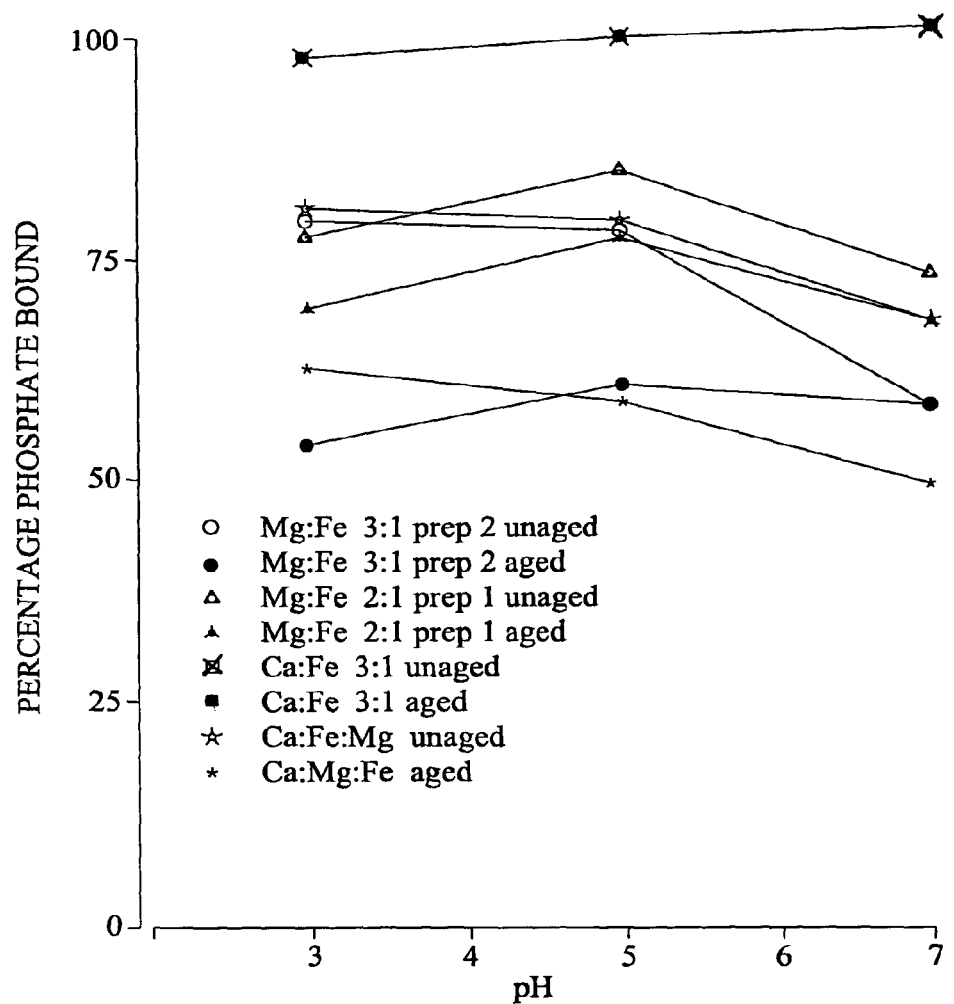

| | | |
|---|---|---|
| 6,733,780 B1 | 5/2004 | Tyler et al. |
| 6,749,864 B2 | 6/2004 | Makino et al. |
| 6,790,895 B2 | 9/2004 | Stelandre et al. |
| 6,794,367 B1 | 9/2004 | Tanida et al. |
| 6,926,912 B1 | 8/2005 | Roberts et al. |
| 2002/0122786 A1 | 9/2002 | Matsuda et al. |
| 2003/0150249 A1 | 8/2003 | Gillman et al. |
| 2003/0185886 A1 | 10/2003 | Lee et al. |
| 2004/0022872 A1 | 2/2004 | Sofue et al. |
| 2004/0105896 A1 | 6/2004 | Roberts et al. |
| 2004/0247696 A1 | 12/2004 | Antelman |
| 2005/0260271 A1 | 11/2005 | Bringley |
| 2008/0187602 A1 | 8/2008 | Ferdinando et al. |

FOREIGN PATENT DOCUMENTS

| | | |
|---|---|---|
| DE | 3346943 A1 | 7/1985 |
| DE | 3402878 A1 | 8/1985 |
| DE | 3801382 A1 | 8/1989 |
| EP | 0050792 A1 | 5/1982 |
| EP | 0146410 A2 | 6/1985 |
| EP | 0150792 A2 | 8/1985 |
| EP | 0368420 A2 | 5/1990 |
| EP | 0638313 A1 | 2/1995 |
| EP | 1304104 A2 | 4/2003 |
| EP | 1413197 A2 | 4/2004 |
| EP | 1932808 A1 | 6/2008 |
| ES | 2018952 A6 | 5/1991 |
| FR | 1214473 A | 4/1960 |
| FR | 2254556 A1 | 7/1975 |
| GB | 1336866 A | 11/1973 |
| GB | 2031395 A | 4/1980 |
| GB | 2254556 A | 10/1992 |
| HU | 173556 B | 6/1979 |
| HU | 201880 B | 1/1991 |
| IN | 192168 A1 | 3/2004 |
| JP | 61036222 A | 2/1986 |
| JP | 62145024 A | 6/1987 |
| JP | 3001114 A | 1/1991 |
| JP | 05155776 A | 6/1993 |
| JP | 05208816 A | 8/1993 |
| JP | 10059842 A | 3/1998 |
| JP | 10101569 A | 4/1998 |
| JP | 10236960 A | 9/1998 |
| JP | 2000086537 A | 3/2000 |
| JP | 2001517633 A | 10/2001 |
| JP | 2004089760 A | 3/2004 |
| PL | 200957 A1 | 4/1978 |
| PL | 189716 A1 | 3/1979 |
| SU | 414849 A1 | 9/1977 |
| WO | WO-91/18835 A1 | 12/1991 |
| WO | WO-92/01458 A1 | 2/1992 |
| WO | WO-94/09798 A1 | 5/1994 |
| WO | WO-95/11033 A1 | 4/1995 |
| WO | WO-95/29679 A1 | 11/1995 |
| WO | WO-96/30029 A1 | 10/1996 |
| WO | WO-97/11166 A1 | 3/1997 |
| WO | WO-97/22266 A1 | 6/1997 |
| WO | WO-97/48380 A1 | 12/1997 |
| WO | WO-99/15189 A1 | 4/1999 |
| WO | WO-99/44580 A1 | 9/1999 |
| WO | WO-00/32189 A1 | 6/2000 |
| WO | WO-01/27069 A1 | 4/2001 |
| WO | WO-01/49301 A1 | 7/2001 |
| WO | WO-03/017980 A1 | 3/2003 |
| WO | WO-03/028706 A1 | 4/2003 |
| WO | WO-03/072084 A1 | 9/2003 |
| WO | WO-03/092658 A1 | 11/2003 |
| WO | WO-2004/016553 A2 | 2/2004 |
| WO | WO-2004/018094 A1 | 3/2004 |
| WO | WO-2005/009381 A2 | 2/2005 |
| WO | WO-2005/012194 A1 | 2/2005 |
| WO | WO-2005/018651 A1 | 3/2005 |
| WO | WO-2005/027876 A1 | 3/2005 |
| WO | WO-2006/085079 A2 | 8/2006 |
| WO | WO-2007/088343 A2 | 8/2007 |
| WO | WO-2008/071747 A1 | 6/2008 |
| WO | WO-2009/016349 A1 | 2/2009 |
| WO | WO-2009/050468 A1 | 4/2009 |

OTHER PUBLICATIONS

Autissier V. et al., "Relative in vitro Efficacy of the Phosphate Binders Lantanum Carbonate and Sevelamer Hydrochloride", Journal of Pharmaceutical Sciences, 2007, vol. 96, No. 10., p. 2818-2826 (online publication date May 11, 2007, after application date).

Hansen et al., Reduction of nitrate to ammonium by sulphate green rust: activation energy and reaction mechanism, Clay Minerals, 33:87-101 (1998).

Playle et al., The in vitro antacid and anti-pepsin activity of hydrotalcite, Pharm. Acta Helv., 49 Nr. 9/10: 298-302 (1974).

Tsuji et al., Hydrotalcites with an extended $Al^{3+}$ -substitution: synthesis, simultaneous TG-DTA-MS study, and their $CO_2$ adsorption behaviors, J. Mater. Res., 8(5):1137-42 (1993).

Dewberry et al., "Lanthanum carbonate: A novel non-calcium containing phosphate binder", *J Am Soc Nephrol*, 8:A2610 (Sep. 1997).

Adachi-Pagano et al., Synthesis of Al-rich hydrotalcite-like compounds by using the urea hydrolysis reaction-control of size and morphology, J. Mater. Chem., 13(8):1988-93 (2003).

Albaaj et al., Hyperphosphataemia in renal failure: causes, consequences and current management, Drugs, 63(6):577-96 (2003).

Ambrogi et al., Intercalation compounds of hydrotalcite-like anionic clays with anti-inflammatory agents, II: Uptake of diclofenac for a controlled release formulation, AAPS PharmSciTech., 3(3):E26 (2002).

Badawy et al., Effect of drug substance particle size on the characteristics of granulation manufactured in a high-shear mixer, AAPS PharmSciTech., 1(4):E33 (2000).

Badreddine et al.,Ion exchange of different phosphate ions into the zinc-aluminium-chloride layered double hydroxide, Materials Lett., 38(6): 391-5 (1999).

Barriga et al., Hydrotalcites as sorbent for 2,4,6-trinitrophenol: influence of the layer composition and interlayer anion, J. Mater. Chem., 12:1027-34 (2002).

Bolhuis et al., Interaction of tablet disintegrants and magnesium strearate during mixing I: effect on tablet disintegration, J. Pharm. Sci., 70(12):1328-30 (1981).

Bolognini et al., Mg/Al mixed oxides prepared by coprecipitation and sol-gel routes: a comparison of their physico-chemical features and performances in m-cresol methylation, Microporous and Mesoporous Materials, 66:77-89 (2003).

Bothwell, Overview and mechanisms of iron regulation, Nutrition Rev., 53:237-45 (Sep. 1995).

Brauner, Das atomgewicht des lanthans, Zeitschrift fur Anorganische Chemie, 33(1):317-21 (1902).

Brouwers et al., Biopharmaceutical tests on antacids: in vitro and in vivo studies, Drugs Under Experiment. Clin. Res., 5:55-61 (1997).

Brouwers et al., De invioed van de toedieningsvorm op de weringsduur en op het pH-Bereik bij antacida: een in-vitro en in-vivo studie,Pharmaceutisch Weekblad, 111:1244-8 (1976) (abstract only).

Brouwers, Liquid Antacids, Pharmaceutisch Weekblad, 110:337-51 (1975) (abstract only).

Budavari et al. (eds.), The Merck Index, pp. 277, 331, and 917, Merck & Co. (1996).

Carlino, Chemistry between the sheets, Chemistry in Britain, pp. 59-62 (Sep. 1997).

Chatelet et al., Competition between monovalent and divalent anions for calcined and uncalcined hydrotalcite: anion exchange and adsorption sites, Colloids and Surfaces A: Physiochemical and Engineering Aspects, 111:167-75 (1996).

Chitrakar et al., Adsorption of phosphate from seawater on calcined MgMn-layered double hydroxides, J. Colloid Interface Sci., 290(1): 45-51 (2005).

Cook, Adaptation in iron metabolism, Am. J. Clin. Nutr., 51(2):301-8 (1990).

Das et al., Adsorption of phosphate by layered double hydroxides in aqueous solutions, Appl. Clay Sci., 32(3-4):252-60 (2006).

(56) References Cited

OTHER PUBLICATIONS de Roy et al., Antionic Clays: Trends in Pillaring Chemistry, chapter 7, pp. 108-169 In: Synthesis of Microporous Mateirals (1992).
de Roy et al., Layered double hydroxides: synthesis and post-synthesis modification, Chapter I and pp. 33-34 In: Rives (ed.), Layered Double Hydroxides: Present and Future, Nova Science Publishers, Inc. (2001).
de Roy et al., Surface Text and Electron Microscopy Studies, pp. 243-244 In: Rives (ed.), Layered Double Hydroxides: Present and Future, Nova Science Publishers, Inc. (2001).
del Arco et al., Effect of the Mg:Al ratio on borate (or silicate)/nitrate exchange in hydrotalcite, J. Solid State Chem., 151(2):272-80 (2000).
del Arco et al., Surface and textural properties of hydrotalcite-like materials and their decomposition products, In: Rouquerol et al. (eds.), Characterization of Porous Solids III, Studies in Surface Science and Catalysis, vol. 87, pp. 507-515 (1994).
Drueke, Lanthanum carbonate as a first-line phosphate binder: the "cons", Semin. Dial., 20(4):329-32 (2007).
Emmett, A comparison of clinically useful phosphorus binders for patients with chronic kidney failure, Kidney Int.,66:S25-S32 (2004).
Erickson et al., A study of structural memory effects in synthetic hydrotalcites using environmental SEM, Materials Lett., 59:226-9 (2005).
European Search Report for European application No. EP 06013811, dated Jun. 27, 2007.
Evans et al., "Structural Aspects of Layered Double Hydroxides" pp. 1-12, In: Duan et al. (eds.), Layered Double Hydroxides, vol. 119, Springer (2006).
Ferreira et al., Thermal decomposition and structural reconstruction effect on Mg Fe based hydrocalcite compounds, J. Solid State Chem., 177:3058-69 (2004).
Frost et al., Thermal decomposition of synthetic hydrotalcites reevesite and pyroaurite, J. Therm. Analysis Calorimetry, 76:217-25 (2004).
Grant et al. (eds.), Grant & Hackh's Chemical Dictionary, 5th edition, McGraw Hill, pp. 571 (1987).
Grubel et al., Interaction of an aluminum-magnesium containing antacid and gastric mucus: possible contribution to the cytoprotective function of antacids, Aliment. Pharmacol. Ther., 11(1):139-45 (1997).
Guillot et al., The use of magnesium-containing phosphate binders in patients with end-stage renal disease on maintenance hemodialysis, Nephron., 30(2):144-7 (1982).
Shin et al., Phosphorus removal by hydrotalcite-like compounds (HTLcs), Water Sci. Technol., 34(1-2):161-8 (1996).
Hansen et al., Formation of synthetic analogues of double metal-hydroxy carbonate minerals under controlled pH conditions: I. The synthesis of pyroaurite and reevesite, Clay Minerals, 25:161-79 (1990).
Hansen et al., Synthesis and characterization of pyroaurite, Appl. Clay Sci., 10(1-2):5-19 (1995).
Hansen et al., The use of glycerol intercalates in the exchange of $CO_3^{2-}$ with $SO_4^{2-}$, $NO^{3-}$ or $C_L$—in pyroaurite-type compounds, Clay Minerals, 26:311-27 (1991).
Hashi et al., Preparation and properties of pyroaurite-like hydroxy minerals, Clays and Clay Minerals, 31(2):152-4 (1983).
He et al., Preparation of Layered Double Hydroxides, Struct. Bond., 119:89-119 (2006).
Hibino et al., Calcination and rehydration behavior of Mg-Fe-CO3 hydrotalcite-like compounds, J. Materials Sci. Lett., 19(16):1403-5 (2000).
Hirahara et al., Synthesis and antacid property of Mg-Fe layered double hydroxide, Nendo Kagaku—J. Clay Sci. Soc. of Japan, 42(2):70-6 (2002).
International Preliminary Report on Patentability for International Application No. PCT/GB2006/000452, dated Aug. 14, 2007.
International Search Report and Written Opinion for International Publication No. WO 2006/085079, dated Dec. 14, 2006.
International Specialty Products, Pharmaceuticals Solid Dosage Forms (2004).
Iranloye et al., Effects of compression force, particle size and lubricants on dissolution rate, J. Pharm. Sci., 67(4):535-9 (1978).
Ishimura et al., "Hyper- and Hypophosphataemia" pp. 149-158, In: Morii et al. (eds.), Calcium in Internal Medicine, Springer (2002).
Kaplan et al., A preference study: calcium acetate tablets versus gelcaps in hemodialysis patients, Nephrol. Nurs. J., 29(4):363-5 (2002).
Kokot et al., A rotating disk study on the rates of hydrotalcite dissolution at 25° C., Pharmazie, 48 (H4):287-9 (1993).
Konorev et al., Selection of the optimal antacid drug in clinical practice, Consilium Medicum, vol. 5 (2003).
Kostura et al., Rehydration of calcined Mg-Al hydrotalcite in acidified chloride-containing aqueous solution, Collect. Czech. Chem. Commun., 72:1284-94 (2007).
Kovanda et al., Thermal behavior of Ni-Mn layered double hydroxide and characterization of formed oxides, Solid State Sci., 5:1019-26 (2003).
Labajos et al., New layered double hydroxides with hydrotalcite structure containing Ni(II) and V(III), J. Materials Chem., 9:1033-9 (1999).
Lazaridis et al., Flotation of metal loaded clay anion exchangers, Part II: the case of arsenates, Chemosphere, 47:319-24 (2002).
Lazaridis et al., Flotation of metal loaded clay anion exchangers, Part II: the case of chromates, Chemosphere, 42:373-8 (2001).
Lazaridis, Sorption removal of anions and cations in single batch systems by uncalcined and calcined Mg-Al-CO3 hydrotalcite, Water Air Soil Pollution, 146:127-39 (2003).
Leinonen et al., Physical and lubrication properties of magnesium stearate, J. Pharm. Sci., 81(12):1194-8 (1992).
Li et al., Enteric-coated layered double hydroxides as a controlled release drug delivery system, Int. J. Pharm., 287(1-2):89-95 (2004).
Li et al., Stoichiometric Synthesis of Pure $MFe_2O_4$ (M = Mg, Co, and Ni) Spinel Ferrites from Tailored Layered Double Hydroxide (Hydrotalcite-Like) Precursors, Chem. Mater., 16(8):1597-602 (2004).
Lin et al., Evaluation of buffering capacity and acid neutralizing-pH time profile of antacids, J. Formos. Med. Assoc., 97:704-10 (1998).
Linares et al., The influence of hydrotalcite and cancrinite type zeolite in acidic aspirin solutions, Microporous and Mesoporous Materials, 74:105-10 (2004).
Llewellyn et al., The binding of bile acids by hydrocalcite and other antacid preparations, Pharmaceutica Acta Helvetiae, 52(1/2):1-5 (1977).
Logham-Adham, Safety of new phosphate binders for chronic renal failure, Drug Safety, 26(15):1093-1115 (2003).
MacCara, Acid neutralization capacity of Canadian antacid formulations, Can. Med. Assoc. J., 132:523-7 (1985).
Marchi et al., Impregnation-induced memory effect of thermally activated layered double hydroxide, Appl. Clay Sci., 13:35-48 (1998).
McCance et al., Absorption and excretion of iron, The Lancet, pp. 680-684 (Sep. 18, 1937).
McIntyre et al., Iron-magnesium hydroxycarbonate (Alpharen): a novel non calcium containing phosphate binder for the treatment of hyperphosphataemia in chronic haemodialysis patients, Nephrol. Dial. Transplant., 22 (suppl 6): vi171, FP452 Poster Session Abstract (Jun. 22, 2007).
Meng et al., Preparation and thermal decomposition of magnesium/iron (III) layered double hydroxide intercalated by hexacyanoferrate (III) ions, J. Mater. Sci., 39:4655-7 (2004).
Meng et al., Preparation of magnetic material containing MgFe2O4 spinel ferrite from a Mg-Fe(III) layered double hydroxide intercalated by hexacyanoferrate(III) ions, Mater.Chem. Phys., 86:1-4 (2004).
Merck Index, p. 969, entries 5694-707.
Miederer et al., Acid neutralization and bile acid binding capacity of hydrocalcite compared with other antacids: an in-vitro study, Chinese J. Digestive Diseases, 4(3):140-6 (2003).
Miyata et al., Physiochemical properties of synthetic hydrotalcites in relation to composition, Clays and Clay Minerals, 28(1):50-6 (1980).

(56) References Cited

OTHER PUBLICATIONS

Murthy et al., Effect of shear mixing on in vitro drug release of capsule formulations containing lubricants, J. Pharm. Sci., 66(9):1215-9 (1977).

Newman et al., Comparative study of some layered hydroxide salts containing exchangable interlayer anions, J. Solid State Chem., 148:26-40 (1999).

O'Donovan et al., Substitution of aluminium salts by magnesium salts in control of dialysis hyperphosphataemia, The Lancet, pp. 880-881 (Apr. 19, 1986).

Oe et al., Long-term use of magnesium hydroxide as a phosphate binder in patients on hemodialysis, Clin. Nephrol., 28(4):180-5 (1987).

Ookubo et al., Hydrotalcites as potential adsorbents of intestinal phosphate, J. Pharm. Sci., 81(11):1139-40 (1992).

Ookubo et al., Preparation and phosphate ion-exchange properties of a hydrotalcite-like compound, Langmuir, 9(5):1418-22 (1993).

Pesic et al., Thermal characteristics of a synthetic hydrotalcite like material, J. Mater. Chem., 2(10):1069-72 (1992).

Playle et al., The in-vitro antacid and anti-pepsin activity of hydrotalcite, Pharm. Acta Helv., 49(9/10):298-302 (1974).

Powell et al., The chemistry between aluminum in the gastrointestinal lumen and its uptake and absorption, Proc. Nutrition Soc., 52:241-53 (1993).

Rajamathi et al., Reversable thermal behaviour of the layered double hydroxide of Mg with Al: mechanistic studies, J. Mater. Chem., 10:2754-7 (2000).

Raki et al., Preparation, Characterization, and Moessbauer Spectroscopy of Organic Anion Intercalated Pyroaurite-like Layered Double Hydroxides, Chem. Mater., 7(1):221-4 (1995).

Reichle, Synthesis of anionic clay minerals (mixed metal hydroxides, hydrotalcite), Solid State Ionics, 22(1):135-41 (1986).

Remuzzi et al., Hematologic consequences of renal failure, Chapter 50, pp. 2079-2101 In: Rose, Pathophysiology of Renal Disease, McGraw-Hill (1987).

Remuzzi et al., Hematologic consequences of renal failure, The Kidney, vol. II, 5th ed. pp. 2170-2186 (1996).

Rives, Study of Layered Double Hydroxides by Thermal Methods, chapter 4, pp. 116-133 In: Rives (ed.), Layered Double Hydroxides: Present and Future, Nova Science Pub Inc. (2001).

Robolot et al., Effect of lubricant level and applied copressional pressure on surface friction of tablets, J. Pharm. Sci., 74(6):697-9 (1985).

Rodriguez-Benot et al., Mild hyperphosphatemia and mortality in hemodialysis patients, Am. J. Kidney Dis., 46(1):68-77 (2005).

Rudnic et al., Oral Solid Dosage Forms, chapter 45, pp. 858-890 In: Gennaro (ed.), Remington: The Science and Practice of Pharmacy, 20th ed., Lippincott Williams & Wilkins (2000).

Sato et al., Adsorption of various anions by magnesium aluminum oxide Mg(0.7)Al(0.3)O(1.15), Ind. Eng. Chem. Prod. Res. Dev., 25:89-92 (1986).

Sato et al., Causticization of sodium carbonate with rock-salt-type magnesium aluminium oxide formed by the thermal decomposition of hydrotalcite-like layered double hydroxide, J. Chem. Tech. Biotechnol., 57:137-40 (1993).

Seida et al., Removal of phosphate by layered double hydroxides containing iron, Water Res., 36:1305-12 (2002).

Sheikh et al., Reducation of dietary phosphorus absorption by phosphorous binders: A theoretical, in vitro, and in vivo study, J. Clin. Invest., 83:66-73 (1989).

Shen et al., Preparation and characterization of Fe/MgO catalysts obtained from hydrotalcite-like compounds, Catalysis Today, 30(1-3):77-82 (1996).

Stamatakis et al., Influence of pH on in vitro disintegration of phosphate binders, Am. J. Kidney Dis., 32(5):808-12 (1998).

Suren, Evaluation of lubricants in the development of tablet formulation, Dansk TIDSskr. Farm 45, pp. 331-338 (1971).

Tezuka et al, The Synthesis and Phosphate Adsorptive Properties of Mg(II)-Mn(III) Layered Double Hydroxides and Their Heat-Treated Materials, Bull Chem. Soc. Jpn. 2004, 77:2101-7 (2004).

The National Kidney Foundation Kidney Disease Quality Outcomes Initiative, Clinical Practice Guidelines for Bone Metabolism and Disease in Chronic Disease, Guide 5 pp. 1, pt. 5.5 (2003).

Tichit et al., Catalysis by hydrotalcites and related materials, Cattech, 7(6):206-17 (2003).

Titulaer et al., The formation of ice between hydrotalcite particles measured by thermoporometry, Clay Minerals, 31(2):263-77 (1996).

Trifiro et al, "Hydrotalcite-like Anionic Clays (Layered Double Hydroxides)", vol. 7, chapter 8, pp. 251-291, In: Alberti et al. (eds.) Comprehensive Supramolecular Chemistry, Pergamon, Oxford (1996).

Ulibarri et al., Kinetics of the thermal dehydration of some layered hydroxycarbonates, Thermochimica Acta, 135:231-6 (1998).

USANA Technical Bulletin, Tablet Excipients, Jun. 1999.

Van Der Voet et al., Intestinal absorption of aluminium from antacids: a comparison between hydrotalcite and algeldrate, Clin. Tech., 24(6):545-3 (1986).

Vatier et al., Antacid activity of calcium carbonate and hydrotalcite tablets, Arzneim-Forsch/Drug Res., 44(4):514-8 (1994).

Vitkova et al., The use of some hydrophobic substances in tablet technology, Milan Chilabala, Acta Pharamceutica Hungaria, 68:336-44 (1998).

Written Opinion for PCT/GB2007/000308, Nov. 30, 2007.

Zhang et al., Phosphorous anion exchange characteristic of a pyroaurite-like compound, Inorg. Mater., 4:132-8 (1997).

Zhang et al., Synthesis and characterization of a novel nanoscale magnetic solid base catalyst involving a layered double hydroxide supported on a ferrite core, J. Solid State Chem., 177:772-80 (2004).

Zhao et al., Preparation of layered double-hydroxide nanomaterials with a uniform crystalite size using a new method involving separate nucleation and aging steps, Chem. Mater., 14(10):4286-91 (2002).

Zhu et al., Adsorption of phosphate by hydrotalcite and its calcined product, Acta Mineralogica Sinica, 25(1):27-32 (2005).

Zhu et al., Different Mg to Fe ratios in the mixed metal MgFe hydroxy-carbonate compounds and the effect on phosphate binding compared with established phosphate binders, J. Pharm. Sci., 91(1):53-66 (2002).

* cited by examiner

Effect of increasing weight of compound on percentage phosphate bound at pH3

Phosphate binding by the calcium ferric iron preparations over the pH range 3-8

Phosphate binding by aluminium hydroxide, magnesium hydroxide and calcium carbonate over the pH range 3-8

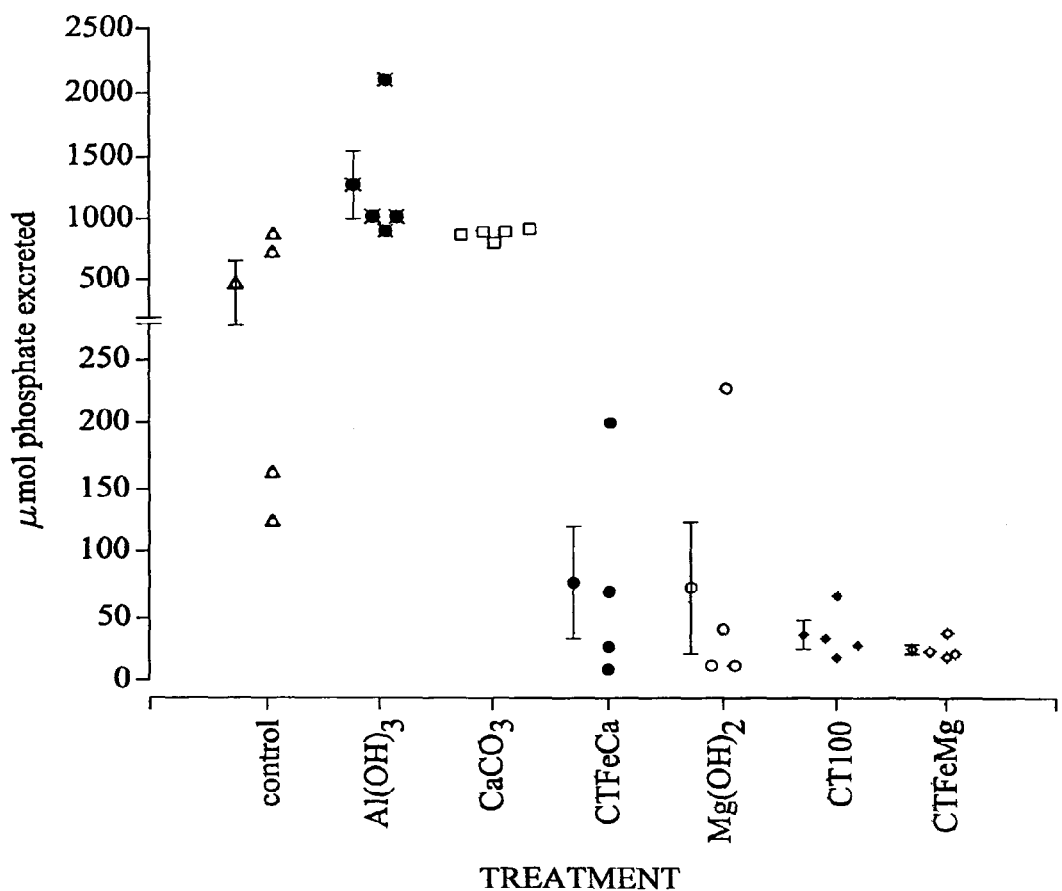

FIG. 9

Individual and mean (±1SEM) urinary phosphate excretion for control rats and those treated with phosphate binding compounds.
Individual values of urinary phosphate excretion (μmol/24 hours) were plotted for controls (△) and animals treated with Al(OH)$_3$(■), CaCO$_3$(□), CTFeCa(●), Mg(OH)$_2$(○), CT100 (♦) and CTFeMg (◇). Mean (±SEM) for each group are presented by points with error bars. *p<0.05 compared to Al(OH)$_3$ treated animal groups.

Mean (+1SEM) soluble faecal phosphate ($g^{-1}$ dry weight as a percentage of total soluble and unsoluble) faecal phosphate ($g^{-1}$ dry weight) for control rats and those treated with phosphate binding compounds.

\* $p<0.05$ compared to control and $CaCO_3$ treated animals
Δ $p<0.05$ compared to $CaCO_3$ treated animals

METAL COMPOUNDS, MIXED OR SULPHATED, AS PHOSPHATE BINDERS

CROSS REFERENCE TO RELATED APPLICATIONS

This application is a divisional of U.S. patent application Ser. No. 10/615,797, filed Jul. 10, 2003 now U.S. Pat. No. 7,799,351, which is a continuation of U.S. patent application Ser. No. 09/508,923, filed on Jun. 19, 2000, issued as U.S. Pat. No. 6,926,912, which is a U.S. National Stage Entry of and claims priority to International Patent Application Serial No. PCT/GB98/02834, filed Sep. 18, 1998, which claims priority to United Kingdom Patent Application Serial No. GB9720061.2, filed Sep. 19, 1997.

This invention relates to metal compounds, especially metal compounds free from aluminium, for pharmaceutical application, especially as phosphate binders.

WO-A-94/09798 discloses mixtures or complexes containing calcium and sulphate for use in a wide variety of pharmaceutical applications. The mixtures or complexes are inorganic compositions derivable from peat, in the form of aqueous solutions or synthetic syngenite ($CaSO_4.K_2SO_4.H_2O$) materials. There is no reference to their phosphate binding capacity.

In patients with kidney failure on haemodialysis (of whom there are 6,000,000 world wide), phosphate concentrations in the blood plasma can rise dramatically and such hyperphosphataemia can result in calcium phosphate deposition in soft tissue. Currently, the plasma phosphate levels are reduced by oral intake of inorganic and organic phosphate binders. The most common treatment in the UK is with aluminum hydroxide gel ("ALUDROX®" at 4 g/day) which forms an insoluble aluminum phosphate. However, this results in further toxic complications due to Al accumulation, e.g. reduction in haemoglobin production, impairment in natural repair and production of bone and possible impairment of neurological/cognitive function. Improvements in phosphate binding capacity as compared with aluminum hydroxide gel have been achieved with other aluminum compounds such as microcrystalline aluminum oxide hydroxide (boehmite) and certain hydrotalcites have been made; Ookubo et al, Journal Pharmaceutical Sciences (November 1992), 81(11), 1139-1140. However, such compounds still result in an intolerable amount of aluminum accumulation in renal failure patients. It is also known to use calcium compounds having poor solubility at pH 6-9, eg calcium carbonate, hydroxide, oxide and/or sulphate in a medicinal form resistant to gastric juices. However, it is known that, for example, with calcium carbonate, a large dosage is required because of its relatively low in vivo capacity for phosphate removal, such large dosages also being difficult to administer. This can cause further complications associated with high calcium intake. It has also been proposed (WO-A-92/01458) to control serum phosphate levels in patients suffering from or predisposed to hyperphosphataemia by contacting ingested phosphate with an oxy-iron compound selected from ferric oxides, oxy-hydroxides and hydroxides. Similarly, Spengler et al, Nephrol. Dial. Transplant. (1996), 11, 808-812, suggests treatment of hyperphosphataemia with a complex of iron (III) oxide-hydroxide modified dextran. However, in the tests conducted, extremely high dosage amounts to animals were given. Moreover, many inorganic preparations are efficient phosphate binders only over a limited pH range, especially an acid pH range of about 3-5. Such current phosphate binders effective at pH3 would not necessarily bind as effectively at higher pH, eg ≥7, which obtain in the lower tract, eg duodenum and below, and where at least some of the binding of phosphate may take place. Moreover, particularly alkaline binders could buffer the stomach pH up to a high level at which they would not have a phosphate binding capacity.

Thus, there is an urgent and widespread need for a phosphate binder which does not release aluminium into the blood stream, which does not provide long term side effects, which can be administered in relatively low dosages and which is effective over a wide pH range of from say 2-8.

We have found surprisingly that certain mixed metal compounds, which are free from aluminium, may bind at least 30% by weight of the total weight of phosphate present over a pH range of from 2-8.

Thus, according to a first aspect, the invention provides a mixed metal compound for pharmaceutical use which is free from aluminium and which has a phosphate binding capacity of at least 30%, by weight of the total weight of phosphate present, over a pH range of from 2-8.

According to a second aspect, the invention provides the use, in the preparation of a medicament for treating hyperphosphataemia, of a mixed metal compound free from aluminium and having a phosphate binding capacity of at least 30%, by weight of the total weight of phosphate present, over a pH range of from 2-8.

Such mixed metal compounds may contain iron (III) and at least one additional metal selected from the group comprising magnesium, calcium, lanthanum and cerium. In one embodiment, the ratio of metal to iron for the compound is at least 1.1:1. In another embodiment, the ratio of metal to iron for the compound is at least 1.3:1. In a further embodiment, the ratio of metal to iron for the compound is at least 1.7:1. In still another embodiment, the ratio of metal to iron for the compound is up to 5:1. In an additional embodiment, the ratio of metal to iron for the compound is up to 2.6:1. In yet another embodiment, the ratio of metal to iron for the compound is up to 2.4:1.

Preferably the mixed metal compounds contain at least one of hydroxyl and carbonate anions and optionally additionally, at least one of sulphate, chloride and oxide.

It is believed that preferred mixed metal hydroxy carbonates containing each of magnesium and iron are of a hydrotalcite structure. For such mixed metal compounds, it is generally preferable to use unaged hydrotalcites, which have not been subjected to a drying operation.

However, it is even more preferable to use mixed calcium/ferric mixed metal compound which seem to be equally effective whether unaged or not.

Even more preferably, the ratio of $Ca^{2+}:Fe^{3+}$ is at least 2:1, still more preferably at least 3:1.

An alternative preferred compound contains $Ca^{2+}$, $Mg^{2+}$ and $Fe^{3+}$, more preferably in a ratio of 3:3:2.

Further investigation of calcium rich compounds led us to find that although anhydrous calcium sulphate as such is a poor phosphate binder, after treatment of calcium sulphate, for example, anhydrous calcium sulphate, with an alkaline material, it became an extremely effective phosphate binder. This result is particularly surprising.

We predict also that each of lanthanum and cerium sulphate will behave similarly.

Thus, according to another aspect, the invention provides metal sulphate material for pharmaceutical use, which metal sulphate material is selected from at least one of calcium, lanthanum and cerium sulphate compounds treated with an alkali solution, preferably an aqueous solution of an alkaline hydroxide, more preferably sodium hydroxide, which said material comprises a solid material, especially a solid material or a suspension of a solid material in a liquid especially aqueous, medium.

According to a further aspect of the invention there is provided the use in a method of preparing a medicament for treatment of hyperphosphataemia of a metal sulphate material selected from at least one of calcium, lanthanum and cerium sulphate compounds treated with an alkali solution.

According to a still further aspect, there is provided a method of preparing a metal sulphate material, which method comprises treating a metal sulphate selected from at least one of calcium, lanthanum and cerium sulphate with an alkali solution.

Preferred embodiments of the invention will now be described in more detail with reference to the following Examples (which also include comparative tests) and graphical representations. In each of FIGS. 1-8, the ordinate (y-axis) gives the percentage of phosphate bound and the abscissa (x-axis) the pH. In the Figures, FIG. 1 shows the effect of pH and ageing on percentage phosphate binding of mixed metal compounds. In FIG. 1,

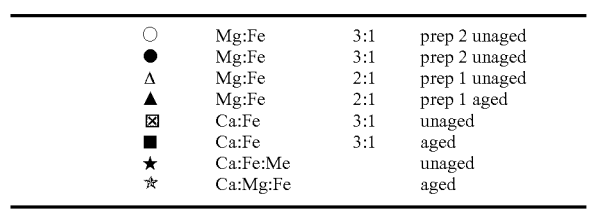

Figure 2:
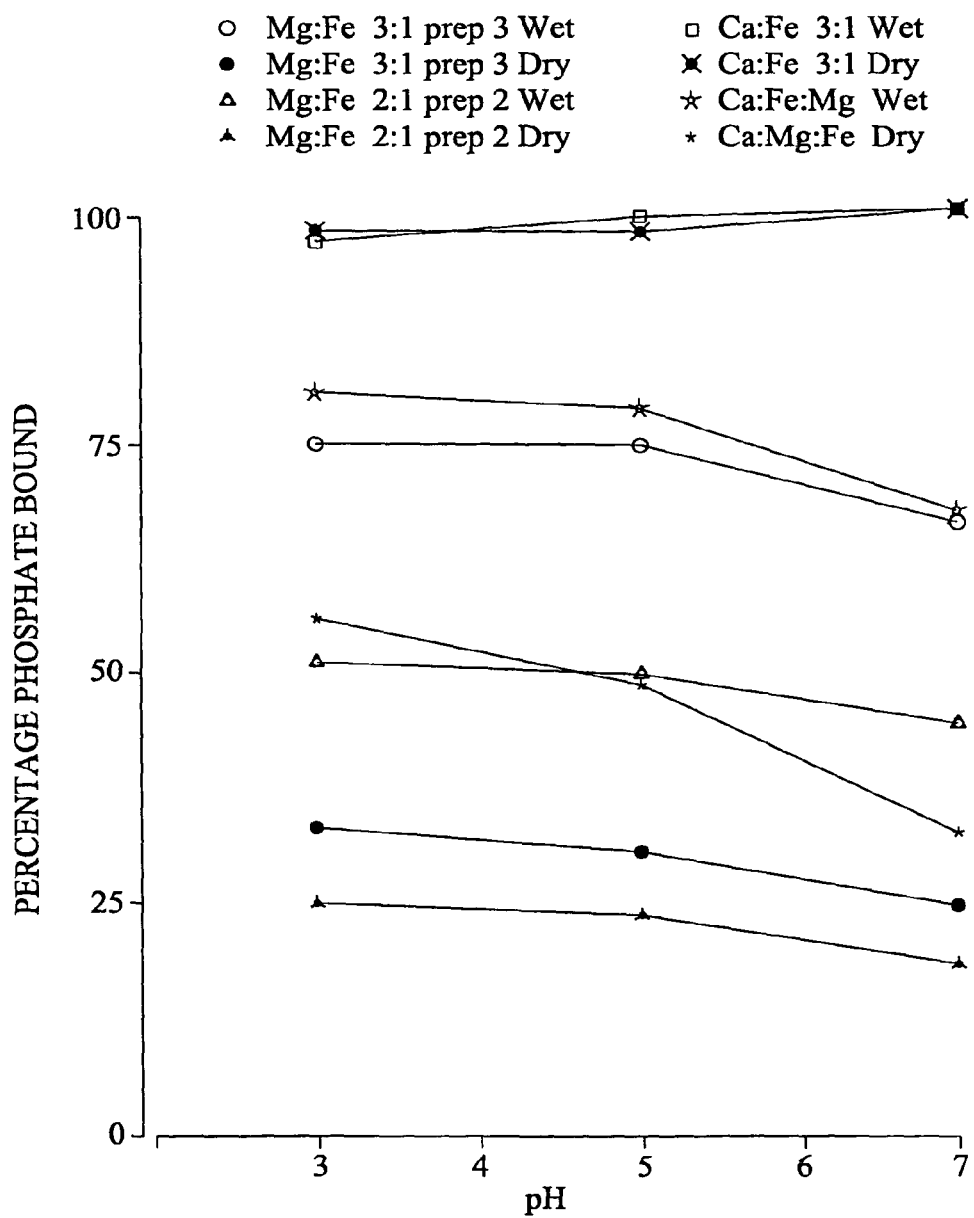

FIG. 2 shows the effect of pH and drying on percentage phosphate binding of mixed metal compounds. In FIG. 2,

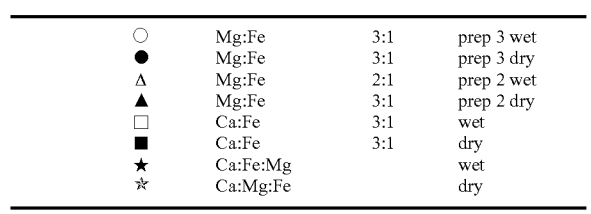

Figure 3:
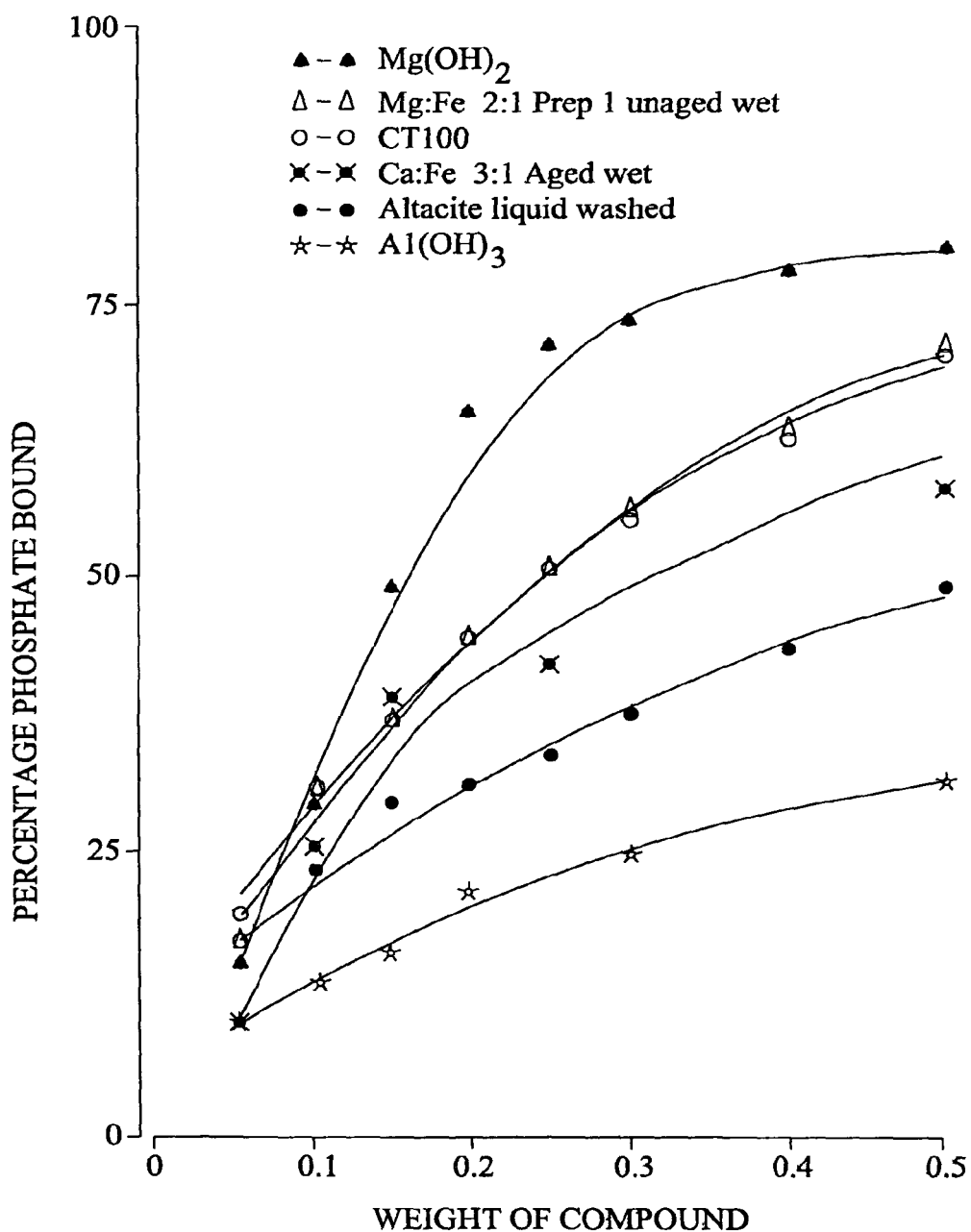

FIG. 3 shows the effect of increasing weight of compound on percentage phosphate bound at pH3. In FIG. 3,

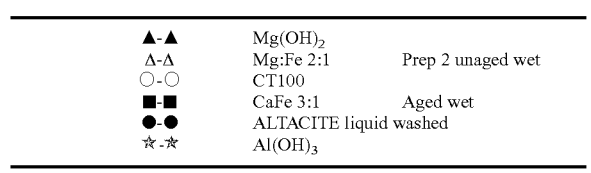

Figure 4:
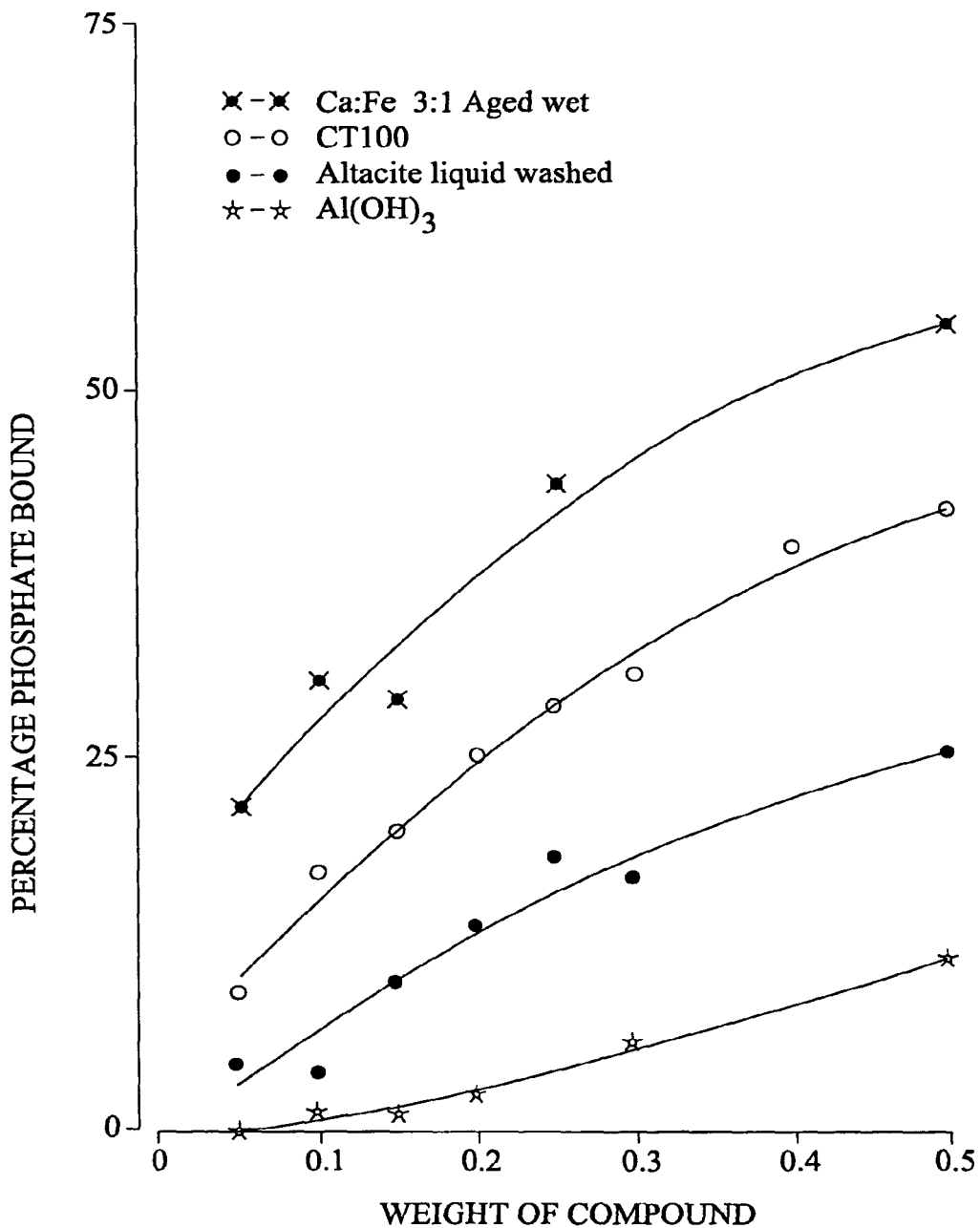

FIG. 4 shows the effect of increasing weight of compound on percentage phosphate bound at pH7. In FIG. 4,

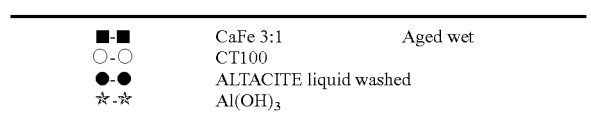

Figure 5:
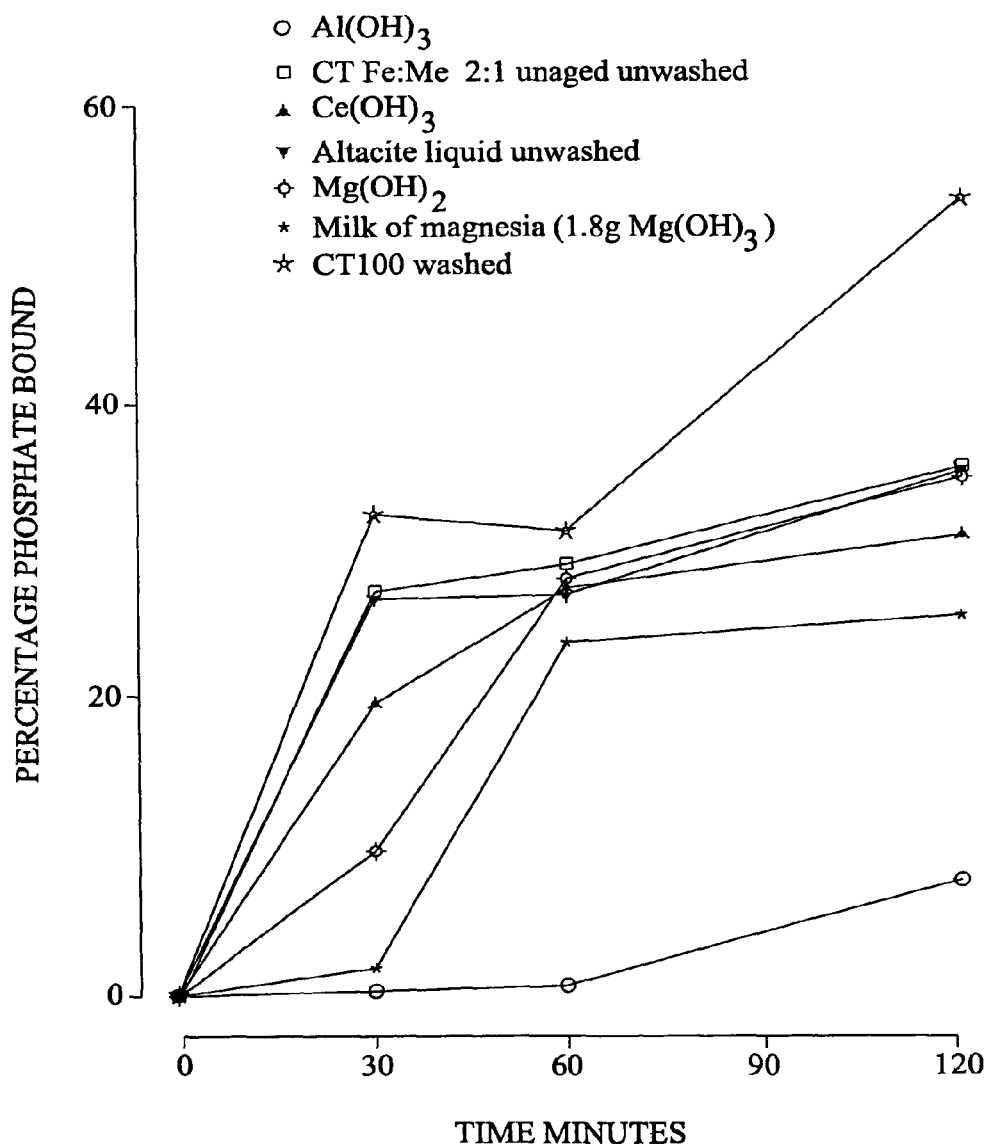

FIG. 5 shows the time course of phosphate binding in food. In FIG. 5,

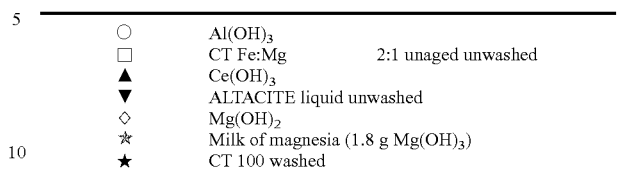

Figure 6:
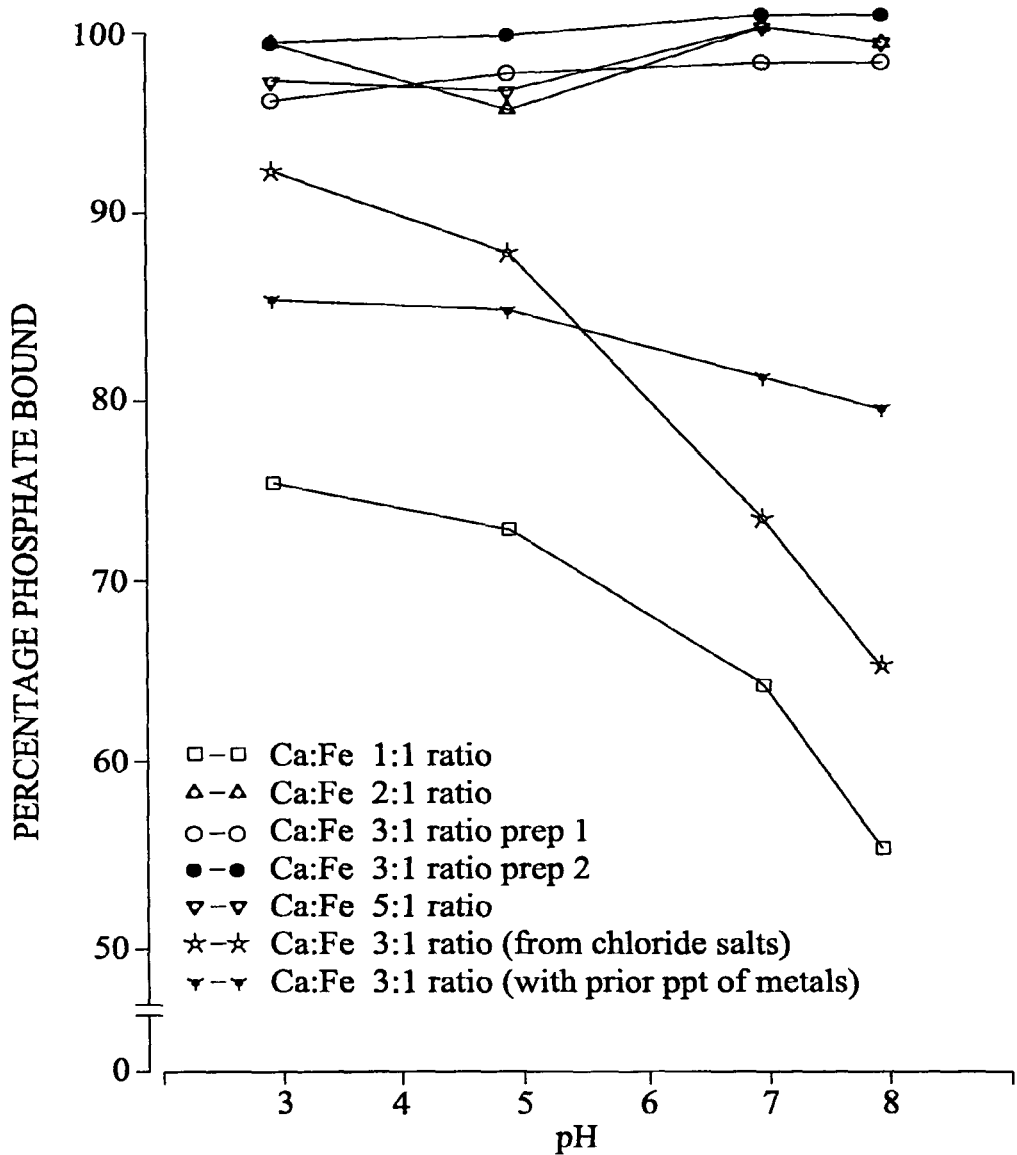

FIG. 6 shows the effect of phosphate binding by the calcium ferric iron preparations over the pH range 3-8. In FIG. 6.

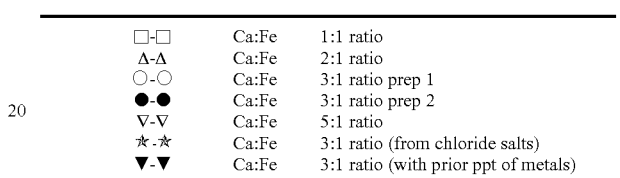

Figure 7:
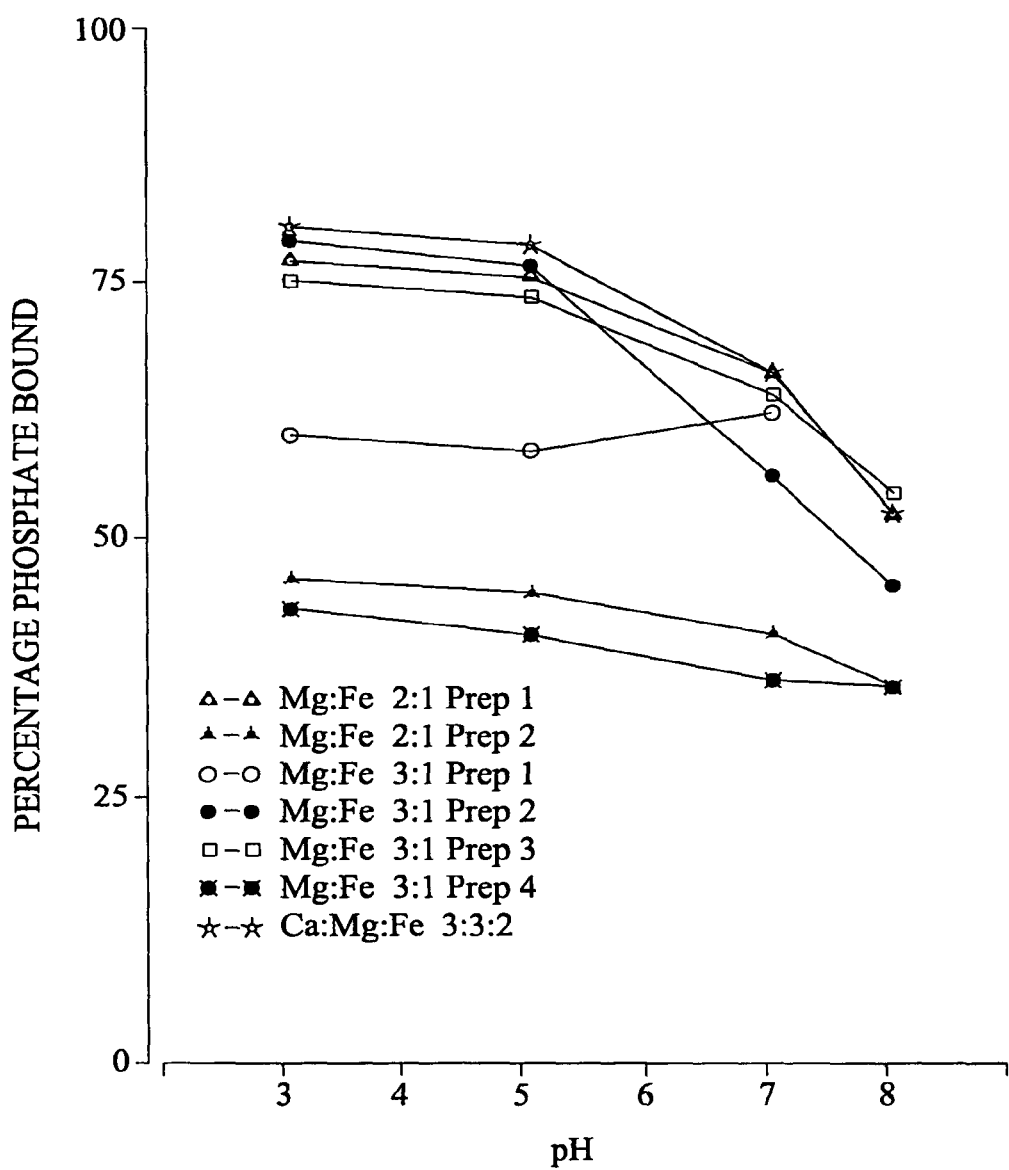

FIG. 7 shows the effect of phosphate binding by the magnesium ferric iron and calcium magnesium ferric iron preparations over the pH range 3-8. In FIG. 7,

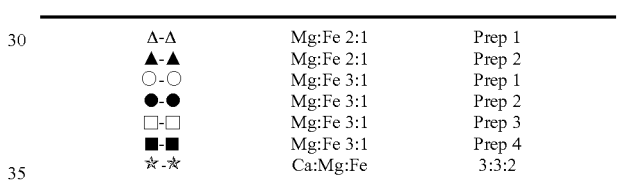

Figure 8:
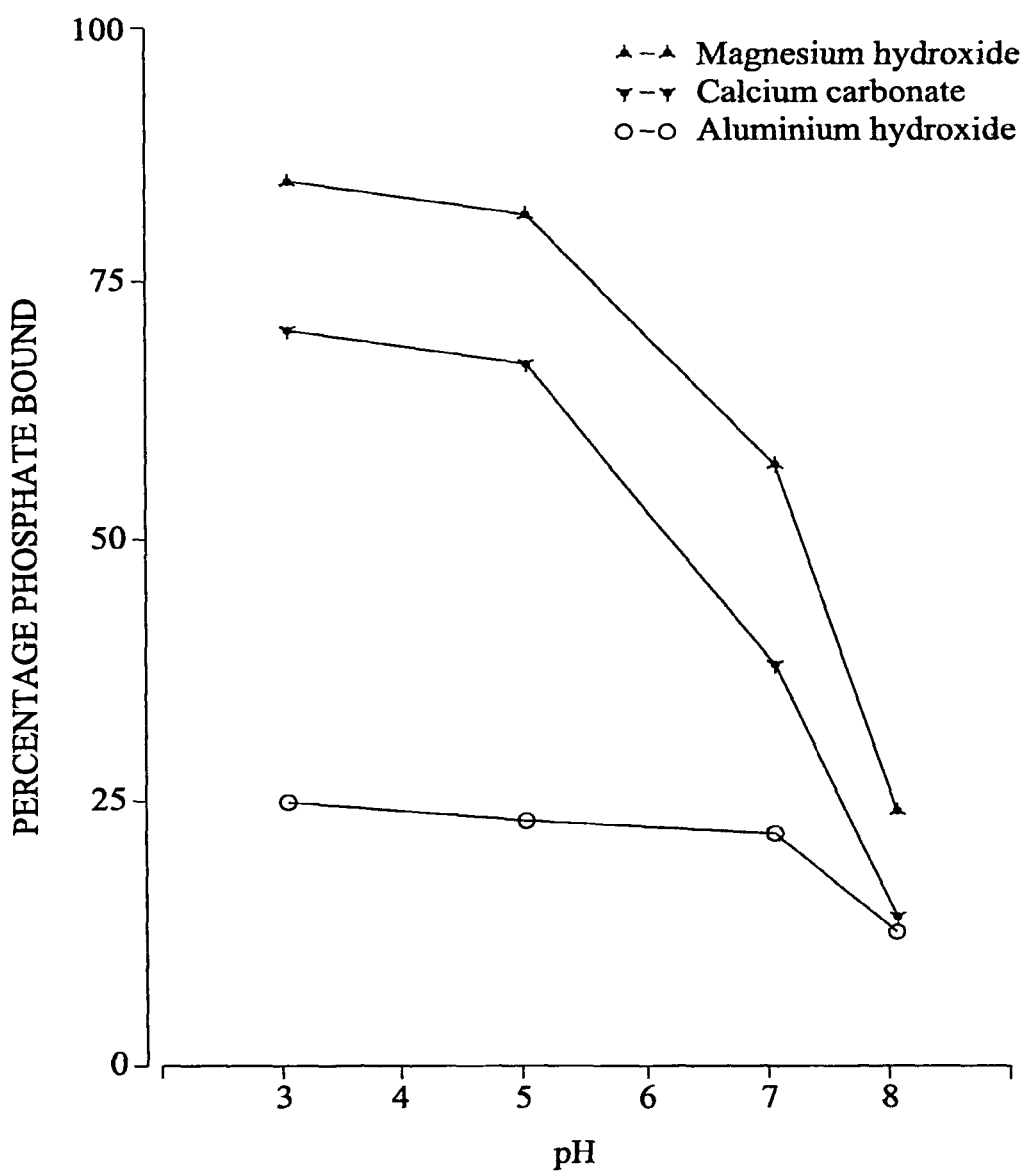

FIG. 8 shows the effect of phosphate binding by aluminium hydroxide, magnesium hydroxide and calcium carbonate over the pH range 3-8. In FIG. 8,

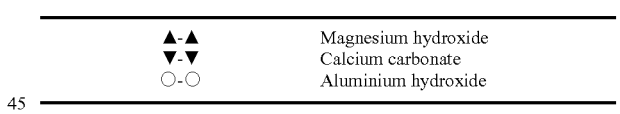

Figure 10:
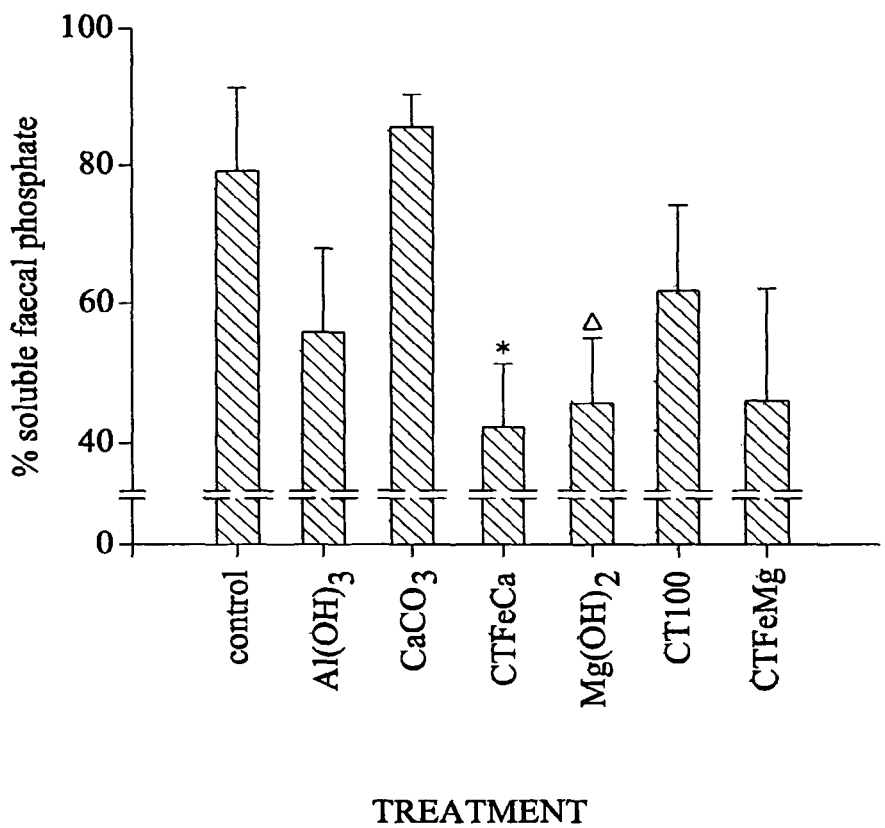

FIG. 9 shows the individual and mean (±1 SEM) urinary phosphate excretion for control rats and those treated with phosphate binding compounds. In particular in FIG. 9, individual values of urinary phosphate excretion (μmol/24 hours) were plotted for controls (Δ) and animals treated with Al(OH)$_3$ (■), CaCO$_3$ (□), CTFeCa (●), Mg(OH)$_2$ (○), CT100 (◆) and CTFeMg (◇). Mean (±SEM) for each group are presented by points with error bars. *p<0.05 compared to Al(OH)$_3$ treated animal groups; and FIG. 10 shows the mean (±1 SEM) soluble faecal phosphate (g$^{-1}$ dry weight) as a percentage of total (soluble and unsoluble) faecal phosphate (g$^{-1}$ dry weight) for control rats and those treated with phosphate binding compounds. In FIG. 10,

*p<0.05 compared to control and CaCO$_3$ treated animals
Δp<0.05 compared to CaCO$_3$ treated animals

EXAMPLE 1

Preliminary Investigation

Compounds listed in Table 1 below, known to be effective phosphate binders were selected for investigation. In Table 1, the values indicate respective percentage phosphate binding capacity at each of pH3, pH7 and pH8, n indicating the number of trials made for each compound. In the Table, CT100 is a hydrotalcite of the formula $Al_2Mg_6OH_{16}.CO_3.4H_2O$, commercially available from Crosfield Limited (UK) and CT2000 is the compound CT100 in the form of an undried slurry.

The phosphate binding capacity was measured by mixing 3.2 mmol of the compound with 25 ml of 20 mmol $l^{-1}$ phosphate buffer for 30 min at 25° C. For all compounds except CT2000, which compounds were dry powders, the compounds were merely weighed and dosed. For CT2000, the slurry was dosed in an amount such as to give an equivalent of 1 g of a powder dried to constant weight at 40° C. Sodium phosphate and sodium hydrogen phosphate were mixed to provide respective phosphate solutions at pH3, 7 and 8 (HCl being added to provide pH3). The binder was separated from the solution by centrifugation (5 min, 3000 rpm) and filtration through 0.22 µm filters, to provide a supernatant, the phosphate content of which was then measured using a 911 Hitachi autoanalyser with Boehringer Mannheim chemistry. The results are shown in Table 1, in which n refers to the number of observations and the values as the % of phosphate precipitated out of solution, calculated as follows:

$$100-[(x/y)\cdot 100]$$

where x=mmol phosphate in solution after precipitation; and y=mmol phosphate in solution without precipitation.

TABLE 1

| Compound | pH3 | pH7 | pH8 |
|---|---|---|---|
| $Al(OH)_3$ (n = 4) | 14.7 + 1.8 | 6.2 + 0.4 | 2.7 + 1.6 |
| $CaCO_3$ (n = 4) | 15.3 + 0.5 | 9.7 + 1.8 | 2.4 + 1.8 |
| $Mg(OH)_2$ (n = 4) | 61.1 + 7.5 | 45.7 + 5.9 | 12.5 + 3.7 |
| $Ce(OH)_3$ (n = 3) | 69.8 + 7.5 | 57.8 + 8.9 | 60.5 + 1.5 |
| CT100 (n = 3) | 94.6 + 1.6 | 91.5 + 2.5 | 91.7 + 0.3 |
| CT2000 (n = 3) | 90.7 + 1.2 | 87.2 + 0.0 | 82.3 + 1.4 |

As can be seen from Table 1, each of the hydrotalcite-like materials had a considerably higher phosphate binding capacity over a wider pH range.

Dosage relationship curves for the CT compounds and $Al(OH)_3$ in pH3, 5 and 7 phosphate buffer showed that the CT compounds bound at least twice as much phosphate as an equivalent weight of $Al(OH)_3$.

$Al(OH)_3$ released as much as 20,000-41,000/µg$^{-1}$ of $Al^{3+}$. Moreover, although the CT compounds released a considerably lower amount (17-66/µg $l^{-1}$), this would still be likely to provide adverse effects in long time-dosage regimes.

Nevertheless, as indicated by Ookubu (supra); it was still thought necessary to include $Al^{3+}$ within the structure of a phosphate binding compound. However, in a test similar to that described above, it was found surprisingly that a compound prepared in a manner similar to that used for preparing CT100 (see Example 3 below) but substituting an equivalent amount of $Fe^{3+}$ gave an excellent phosphate binding capacity, especially at pH3 where a ~70% phosphate binding capacity was achieved, without the risk of release of any aluminium.

EXAMPLE 2

Comparison of Mixed Metal Hydroxy Carbonates

Compounds Tested:
(1) a hydroxy carbonate containing a 2:1 ratio Mg:Fe
(2) a hydroxy carbonate containing a 3:1 ratio of Mg:Fe
(3) a hydroxy carbonate containing a 3:1 ratio of Ca:Fe
(4) a hydroxy carbonate containing a 3:3:2 ratio of Ca:Mg:Fe
(5) CT100, a hydrotalcite of the formula $Al_2Mg_6(OH)_{16}CO_3.4H_2O$, commercially available from Crosfield Limited.
(6) ALTACITE, a hydrotalcite of the same formula as CT100, commercially available from Roussell, in the form of an aqueous slurry
(7) magnesium hydroxide
(8) aluminium hydroxide Methods of Measuring Phosphate Binding Capacity As indicated below, the following methods of measuring phosphate binding capacity were adopted:

Method 1—1 gram of each phosphate binder compound (taking hydration of the wet cake compound into account) was added to 25 ml, 40 mmol $l^{-1}$ sodium phosphate buffer adjusted to pH 3, pH 5 or pH 7 as described in Example 3 below. Samples were whirl mixed to ensure homogeneity and gently agitated at room temperature for 30 minutes. Following centrifugation for 5 min at 3000 rpm, the supernatant was filtered through 0.22 µm millipore filters. Soluble phosphate was measured in the supernatant. The percentage phosphate bound by the hydrotalcite was calculated.

Method 2—As method 1 but using 20 mmol $l^{-1}$ phosphate buffer.

Method 3—Milk (250 ml), cornflakes (50 g), bread (2 slices) and MARMITE (yeast extract) (5 g) were mixed in a stomacher for 30 minutes containing 0.01M HCl (so as to simulate the conditions in the stomach). A 20 ml aliquot of food was removed and centrifuged. Phosphate was measured in the supernatant. Two grams of the phosphate binder compound was added to the bulk food slurry and mixed for a further 30 minutes. An aliquot of food was taken and the phosphate measured in the supernatant following centrifugation. Further aliquots were taken after a further 30 and 90 minutes mixing.

In each of the above methods, for each of compounds (1)-(4), where a dry powder was dosed as the phosphate binder, phosphate binding was measured for a given dosage measured after drying to constant weight at 40° C. Where a wet cake was dosed (or ALTACITE (6) added), an amount equivalent to a given constant dry weight at 40° C. was used. For known commercially available binders, a given weight of the material supplied was used.

Results

EXPERIMENT 1

Effect of pH and Ageing on Percentage Phosphate Binding of Mixed Metal Compounds Phosphate binding compounds were prepared in the form of a wet slurry. Unaged samples were obtained by filtering and washing the wet slurry to form a wet cake which was tested in this form, while aged samples were obtained by heating the wet slurry to 80° C. for two hours prior to filtering of the cake, which was then tested. The percentage phosphate binding of the compounds when used aged or unaged across the pH range 3-7 was investigated in this manner.

Method 1 was used for measuring phosphate binding capacity. The results are shown in FIG. 1.

The Ca:Fe 3:1 compound (3) bound almost 100% of the phosphate independently of pH. There was no difference between the aged and unaged compound.

The Mg:Fe compounds (1) and (2) in a 2:1 (prep 1) and 3:1 (prep 2) ratio respectively bound phosphate independently of pH over the range 3-7. The unaged compounds were better phosphate binders than the aged compounds at pH 3-7.

The Ca:Mg:Fe compound (3) also bound phosphate independently of pH; again the unaged was better than the aged compound.

EXPERIMENT 2

Effect of pH and Drying on Percentage Phosphate Binding of Mixed Metal Compounds The percentage phosphate binding of the compounds when used in the dry powder or wet (cake) form across the pH range 3-7 was investigated.

Method 1 was used for measuring phosphate binding capacity. The results are shown in FIG. 2.

Unaged compounds were compared in their wet (cake) form or following drying to constant weight. One gram weight of each compound was used for comparison (hydration of the wet (cake) compound was accounted for e.g. if the hydrotalcite was 20% dry weight (calculated on a constant dry weight at 40° C.), 5 grams were used).

In all cases, except the Ca:Fe 3:1 compound (3), where there was no difference, the wet (cake) form of the compound was a better phosphate binder than the dry powder form. Whether in the wet or dry form, all of the compounds (1)-(4) bound phosphate independently of pH. Similar results are obtained when using aged compounds in that the wet compound bound more phosphate than the dry powder compound.

EXPERIMENT 3

Effect of Increasing Amount of Phosphate Binder Compound on Percentage Phosphate Binding for Various Compounds at pH 3

Method 2 was used for measuring phosphate binding capacity. The results are shown in FIG. 3.

At pH 3, $Mg(OH)_2$, compound (7), was the best phosphate binder. Other studies have however showed this binding is pH dependent, binding almost no phosphate at pH 8. It would therefore have limited use in vivo.

The compounds Mg:Fe 2:1 (1), Ca:Fe 3:1 (2) and CT100 (5) all bound up to 60-70% of the phosphate. Interestingly, the CT100 bound ~50% more phosphate at any weight than the ALTACITE (6), despite an identical molecular formulae.

$Al(OH)_3$ the phosphate binder often used to control serum phosphate levels was relatively ineffective at the range of weights tested.

EXPERIMENT 4

Effect of Increasing Amount of Phosphate Binder Compound on Percentage Phosphate Binding for Various Binders at pH 7

Method 2 was used for measuring phosphate binding capacity. The results are shown in FIG. 4.

At pH 7, the Mg:Fe 3:1 compound (2) was the best phosphate binder over the range of weights studied. The CT100 (5) bound at least twice as much phosphate than the ALTACITE (6) at any weight studied.

EXPERIMENT 5

Phosphate Binding in Food

Method 3 was used for measuring phosphate binding capacity. The results are shown in FIG. 5.

The results show that in food, the CT100 (5) was the best phosphate binder, followed by the Fe:Mg 2:1 compound (2). Again, aluminium hydroxide (8) was ineffective. Interestingly, magnesium hydroxide (7), the best phosphate binder at pH 3, is not the best when used in food. This is probably due to the buffering effect of the food, the initial pH of the slurry being ~5. It therefore shows the pH dependency of using magnesium hydroxide as a phosphate binder.

SUMMARY

Overall, the results demonstrated:

The Mg:Fe and Ca:Fe compounds (1)-(4) were efficient phosphate binders across a range of pH's likely to be found in the gastrointestinal tract.

Phosphate binding by the MgFe and MgCaFe compounds (1), (2) and (4) but not the CaFe compound (3) was reduced by ageing the compounds.

Drying the MgFe and MgCaFe compounds (1), (2) and (4) but not the CaFe compound (3) reduced their phosphate binding.

The known hydrotalcite compound CT100 (5) bound phosphate in food in vitro studies. It also reduced urinary phosphate excretion when given in vivo to normal individuals. However, as the new compounds (1)-(4) bound phosphate in water at least as well as CT100 (5) and a number of times better than $Al(OH)_3$ (8), we would expect they would also bind phosphate in vivo. These compounds have the added benefit of not releasing aluminium.

These new compounds (1)-(4) have a therapeutic potential in the control of serum phosphate levels in patients with end stage renal failure.

EXAMPLE 3

Further Investigations of Phosphate Binding Capacity

Method of Preparation and Measurement

In the following experiments, all chemicals were GPR grade, obtained from BDH. Millipore filters were obtained from Amicon, High Wycombe.

M1. Production of Metal Co-Precipitate Preparations

All preparations were synthesised using the following method which, for a 3:1 ratio of $Mg^{2+}:Al^{3+}$ as respective cations $M^{2+}:M^{3+}$, resulted in the production of the hydrotalcite $Al_2Mg_6(OH)_{16}.CO_3.4H_2O$.

Use of calcium or magnesium as the $M^{2+}$ cation and ferric iron as the $M^{3+}$ cation allowed variations on the above theme to be achieved. By changing the ratio of the $M^{2+}:M^{3+}$ cations to 1:1, 2:1, 3:1 and 5:1, different composition materials could be produced. All compounds however had $CO_3^{2-}$ as the exchangeable anion.

For a 3:1 $M^{2+}:M^{3+}$ ratio, salt containing 2 moles of $M^{3+}$ and salt containing 6 moles of $M^{2+}$ were dissolved in 4 liters de-ionised water. In a separate 4 liters, 16 moles NaOH and 5 moles $Na_2CO_3$ were dissolved. Both solutions were pumped using peristaltic pumps into a flask with an overflow at ~2 liters and constantly mixed. The rate of addition of the solutions was such that the mixed solution had a pH of 10.0-10.5. After discarding the first liter, by which time a steady state had been established, 3-4 liters of overflowing slurry was collected. This was then vacuum filtered using a Buchner, washed with de-ionised water and re-filtered leaving a wet 'cake'.

Preparation names and the solution/suspension compositions used for their production are shown in Table 2. Due to the insolubility of calcium sulphate, when used as the $M^{2+}$ salt, constant stirring was necessary to prevent settling.

M2. Production of a Metal Precipitate Mixture

The metals in the solutions/suspensions described in Table 2 were precipitated at the same time by the addition of sodium hydroxide. A preparation was also made by precipitating the calcium and iron separately with sodium hydroxide, the precipitates were then mixed. For this, $Fe_2(SO_4)_3$ (1 mole) and NaOH (6 moles) were mixed in 4 liters de-ionised $H_2O$. In a separate 4 liters of water, $CaSO_4$ (6 moles), NaOH (12 moles) and $Na_2CO_3$ (5 moles) were mixed. These two suspensions were then fed with into the flask with an overflow at ~2 liters and constantly mixed.

It proved impossible to alter the rate of addition of the precipitate suspensions such that the mixture had a pH of 10.0-10.5. The pH of the mixture fluctuated between ~11.5 and 12.5. After discarding the first liter, 3-4 liters of overflowing slurry was collected. This was then vacuum filtered using a Buchner, washed with de-ionised water and re-filtered leaving a wet 'cake'.

M3. Measurement of Metal Composition

Preparations were washed and dried to constant dry weight in an oven at –40° C. One gram was titrated against 1M HCl until a constant pH of 1 was attained. The concentrations of $M^{2+}$ $M^{3+}$ ions in solution were measured. For iron and calcium a Hitachi 911 autoanalyser with Boehringer Mannheim chemistry was used, while for magnesium a flame photometric atomic absorption spectroscopy was employed.

NB. Although the methods of analysis adopted here were of high accuracy, the method of sampling was such as to provide only an initial approximate assessment of the actual composition; in the results given below, compare the ratios predicted from the proportions of starting materials assuming 100% yield) with those of the final preparations measured in this manner.

M4. Measurement of Phosphate Binding

Phosphate binding for the compounds prepared above, when dosed as a dry powder, was measured in each case at a dosage of 1.0 gram dry weight (determined by drying to constant weight at 40° C.). Where a wet cake was dosed, an amount equivalent to a 1 g dry weight was added. Phosphate binding of the conventional binders, magnesium hydroxide, aluminium hydroxide and calcium carbonate was also measured, in these cases using 1 g of material as supplied.

Phosphate binding capacity was determined over a pH range 3-8, approximately the range of pH's found in the normal gastrointestinal tract. 40 mmol $l^{-1}$ sodium phosphate buffers at pH 5, pH 7 and pH 8 were produced by mixing appropriate volumes of 40 mmol 1 $Na_2HPO_4$ and 40 mmol $l^{-1}$ $NaH_2PO_4$ solutions. A pH 3 phosphate solution was produced by addition of 1 M HCl to a 40 mmol $l^{-1}$ $NaH_2PO_4$ solution.

Preparations were suspended in 25 ml 40 mmol $l^{-1}$ phosphate buffer and whirl mixed to ensure homogeneity. This suspension was then gently agitated at room temperature for 30 minutes followed by centrifugation at 3000 rpm for 5 min. Following filtration of the supernatant through 0.22 µm millipore filters, soluble phosphate was measured using a 911 Hitachi autoanalyser with Boehringer Mannheim chemistry.

Phosphate bound was calculated as a percentage of that present in the original solution.

The compositions of solutions used to produce the metal co-precipitate preparations are shown in Table 2 below.

TABLE 2

Composition of solutions used to produce the metal co-precipitate preparations

| Material name | Moles $M^{2+}$ salt | Moles $M^{3+}$ salt | Moles NaOH | Moles $Na_2CO_3$ |
|---|---|---|---|---|
| Mg:Fe 2:1 (Prep 1) | 4 Mole $MgSO_4$ | 1 Mole $Fe_2(SO_4)_3$ | 12 | 5 |
| Mg:Fe 2:1 (Prep 2) | 4 Mole $MgSO_4$ | 1 Mole $Fe_2(SO_4)_3$ | 12 | 5 |
| Mg:Fe 3:1 (Prep 1) | 6 Mole $MgSO_4$ | 1 Mole $Fe_2(SO_4)_3$ | 16 | 5 |
| Mg:Fe 3:1 (Prep 2) | 6 Mole $MgSO_4$ | 1 Mole $Fe_2(SO_4)_3$ | 16 | 5 |
| Mg:Fe 3:1 (Prep 3) | 6 Mole $MgSO_4$ | 1 Mole $Fe_2(SO_4)_3$ | 16 | 5 |
| Mg:Fe 3:1 (Prep 4) | 6 Mole $MgSO_4$ | 1 Mole $Fe_2(SO_4)_3$ | 16 | 5 |
| Ca:Fe 1:1 | 2 Mole $CaSO_4$ | 1 Mole $Fe_2(SO_4)_3$ | 8 | 5 |
| Ca:Fe 2:1 | 4 Mole $CaSO_4$ | 1 Mole $Fe_2(SO_4)_3$ | 12 | 5 |
| Ca:Fe 3:1 (Prep 1) | 6 Mole $CaSO_4$ | 1 Mole $Fe_2(SO_4)_3$ | 16 | 5 |
| Ca:Fe 3:1 (Prep 2) | 6 Mole $CaSO_4$ | 1 Mole $Fe_2(SO_4)_3$ | 16 | 5 |
| Ca:Fe 5:1 | 10 Mole $CaSO_4$ | 1 Mole $Fe_2(SO_4)_3$ | 24 | 5 |
| Ca:Fe 3:1 (made with chloride salts) | 6 Mole $CaCl_2$ | 2 Mole $FeCl_2$ | 16 | 5 |
| Ca:Mg:Fe 3:3:2 | 3 Mole $MgSO_4$ 3 Mole $CaSO_4$ | 1 Mole $Fe_2(SO_4)_3$ | 16 | 5 |

Results

The following results were obtained.

R1. Predicted and Measured Metal Compositions of the Preparations

To determine if the ratio of metal ions in the original solutions was also present in the end preparation, all materials were hydrolysed with 1M HCl and the solution metal ion concentrations measured. The results are shown in Table 3 below. These show that the compounds prepared as above were indeed mixed metal compounds.

TABLE 3

Predicted and measured metal compositions of the preparations

| Material name | Predicted $M^{2+}:M^{3+}$ ratio | Measured $M^{2+}:M^{3+}$ ratio |
|---|---|---|
| Mg:Fe 2:1 (Prep 2) | 2:1 | 1.7:1 |
| Mg:Fe 3:1 (Prep 1) | 2:1 | 2.4:1 |
| Mg:Fe 3:1 (Prep 2) | 3:1 | 2.2:1 |
| Mg:Fe 3:1 (Prep 3) | 3:1 | 2.2:1 |
| Mg:Fe 3:1 (Prep 4) | 3:1 | 2.3:1 |
| Ca:Fe 1:1 | 1:1 | 1.3:1 |
| Ca:Fe 2:1 | 2:1 | 1.6:1 |
| Ca:Fe 3:1 (Prep 2) | 3:1 | 2.6:1 |
| Ca:Fe 5:1 | 5:1 | 1.3:1 |
| Ca:Fe 3:1 (made with Cl– salts) | 3:1 | 1.4:1 |
| Ca:Fe 3:1 (mixing of metals after ppt″) | 3:1 | 1.1:1 |
| Ca:Mg:Fe | 3:3:2 | 2.9:2.3:2 |

R2. Phosphate Binding

R2.1. Calcium and Ferric Iron Containing Preparations

The preparations containing different ratios of calcium to ferric iron were tested for their capacity to bind phosphate.

The reproducibility of results was demonstrated with reference to a predicted $Ca^{2+}:Fe^{3+}$ ratio of 3:1 and this is shown in Table 4 below, while the results obtained for different ratios are shown in FIG. 6 and Table 5 below.

In the graphs shown FIG. 6, values plotted are the mean of the two separate experiments.

(i) A Predicted $Ca^{2+}:Fe^{3+}$ Ratio of 3:1

Two different calcium ferric iron preparations with a predicted 3:1 ratio were synthesised. When preparation 2 was hydrolysed, elemental analysis showed the measured calcium to ferric iron ratio to be 2.6:1. Insufficient sample of preparation 1 was available for hydrolysis.

Phosphate binding by each preparation was tested in two separate experiments across the pH range 3-8. Binding was reproducible for both preparations at each pH (Table 4). At least 96% of the phosphate present in solution was bound by each preparation at each pH (FIG. 5, Table 4).

TABLE 4

Reproducibility of phosphate binding for preparations with a predicted 3:1 $Ca^{2+}:Fe^{3+}$ ratio

| | Percentage phosphate binding at | | | |
|---|---|---|---|---|
| | pH 3 | pH 5 | pH 7 | pH 8 |
| Prep 1 (exp. 1) | 97 | 98 | 98 | 97 |
| Prep 1 (exp. 2) | 96 | 96 | 97 | 97 |
| Prep 2 (exp. 1) | 98 | 99 | 100 | 100 |
| Prep 2 (exp. 2) | 100 | 99 | 100 | 99 |

(ii) A Predicted $Ca^{2+}:Fe^{3+}$ Ratio of 1:1

One calcium ferric iron preparation with a predicted 1:1 ratio was synthesised. Elemental analysis of the hydrolysed material showed the measured calcium to ferric iron ratio to be 1.3:1.

Greater than 50% of the phosphate present in solution was bound by the preparation at pH 3-8 (FIG. 6, Table 5). Phosphate binding was pH dependent. The material bound 28% less phosphate at pH 8 than at pH 3.

(iii) A Predicted $Ca^{2+}:Fe^{3+}$ Ratio of 2:1

One calcium ferric iron preparation with a predicted 2:1 ratio was synthesised. Elemental analysis of the hydrolysed material showed the measured calcium to ferric iron ratio to be 1.6:1.

At least 97% of the phosphate present in solution was bound over the pH range 3-8 (FIG. 6, Table 5). There was no pH dependency of the binding.

(iv) A Predicted $Ca^{2+}:Fe^{3+}$ Ratio of 5:1

One calcium ferric iron preparation with a predicted 5:1 ratio was synthesised. Elemental analysis of the hydrolysed material showed the measured calcium to ferric iron ratio to be 1.5:1.

At least 95% of the phosphate present in solution was bound over the range pH 3-8 (FIG. 6, Table 5). There was no pH dependency of the binding.

(v) A Predicted $Ca^{2+}:Fe^{3+}$ Ratio of 3:1 Made Using Metal Chloride Salts

Due to the insolubility of calcium sulphate, a preparation was made using the soluble salt, calcium chloride. One calcium ferric iron preparation with a predicted 3:1 ratio was synthesised. Elemental analysis of the hydrolysed material showed the measured calcium to ferric iron ratio to be 1.4:1.

Greater than 60% of the phosphate present in solution was bound over the pH range 3-8 (FIG. 6, Table 5). Phosphate binding was pH dependent with 31% less precipitated at pH 8 than pH 3.

(vi) A Predicted $Ca^{2+}:Fe^{3+}$ Ratio of 3:1 Made by Precipitating the Calcium and Iron Prior to Mixing A preparation was made to determine whether precipitation of calcium and ferric iron from their sulphates prior to mixing would produce a phosphate binding material. This compound was prepared as in methods M2. The predicted ratio of calcium to ferric iron was 3:1 although, the ratio measured following acid hydrolysis was 1.1:1.

Greater than 75% of the phosphate present in solution was bound over the pH range 3-8 (FIG. 6, Table 5). The binding was pH dependent to a small degree, at pH 8, 8% less phosphate was bound than at pH 3.

TABLE 5

Phosphate binding by the calcium ferric containing preparations at pH 3-8

| Predicted $Ca^{2+}:Fe^{3+}$ ratio | Percentage phosphate bound | | | |
|---|---|---|---|---|
| | pH 3 | pH 5 | pH 7 | pH 8 |
| 1:1 | 75 | 72 | 63 | 54 |
| 2:1 | 99 | 95 | 99 | 98 |
| 3:1* | 98 | 99 | 100 | 100 |
| 5:1 | 97 | 96 | 99 | 98 |
| 3:1 (made with chloride salts) | 92 | 87 | 72 | 64 |
| 3:1 (with prior ppt" of metals) | 85 | 84 | 80 | 78 |

*Preparation 2 (exp. 1) of Table 4 also included for comparison

R2.2 Preparations Containing Magnesium and Ferric Iron

A number of preparations containing different ratios of magnesium to ferric iron were tested for their ability to bind phosphate.

The reproducibility of results was demonstrated in each case and these results are shown in Tables 6-8 below, while a comparison of the results is shown in FIG. 7.

(i) A Predicted $Mg^{2+}:Fe^{3+}$ Ratio of 3:1

Four magnesium ferric iron preparations were synthesised with the predicted ratio of 3:1. Preparation 1 had an actual $Mg^{2+}:Fe^{3+}$ ratio of 2.4:1 Preparations 2, 3 and 4 had measured $Mg^{2+}:Fe^{3+}$ ratios of 2.2:1, 2.2:1 and 2.3:1 respectively.

Preparation 1 bound at least 60% of the phosphate over the pH range 3-7. Preparations 2, 3 and 4 bound at least 40%, 50% and 30% of the phosphate respectively over the pH range 3-8 (FIG. 7, Table 6). Phosphate binding by preparation 4 was reproducible (Table 6). A shortage of material meant binding experiments on preparations 1, 2 and 3 were carried out once.

The three preparations studied over the pH range 3-8 all displayed pH dependency in their phosphate binding. Preparations 2 and 3 bound 44% and 29% less phosphate respectively at pH 8 than pH 3. Preparation 4 bound a mean of 21% less phosphate at pH 8 than pH 3.

TABLE 6

Phosphate binding for preparations with the predicted 3:1 $Mg^{2+}:Fe^{3+}$ ratio

| | Percentage phosphate binding at | | | |
|---|---|---|---|---|
| | pH 3 | pH 5 | pH 7 | pH 8 |
| Prep 1 | 60 | 58 | 61 | — |
| Prep 2 | 79 | 76 | 55 | 44 |
| Prep 3 | 75 | 73 | 63 | 53 |

TABLE 6-continued

Phosphate binding for preparations with the predicted 3:1 $Mg^{2+}:Fe^{3+}$ ratio

| | Percentage phosphate binding at | | | |
|---|---|---|---|---|
| | pH 3 | pH 5 | pH 7 | pH 8 |
| Prep 4 (exp. 1) | 41 | 40 | −34 | 37 |
| Prep 4 (exp. 2) | 45 | 39 | 36 | 32 |

(i) A Predicted $Mg^{2+}:Fe^{3+}$ Ratio of 2:1

Two magnesium ferric iron preparations with a predicted 2:1 ratio were synthesised. Elemental analysis of preparation 2 following hydrolysis showed the measured magnesium to ferric iron ratio to be 1.7:1. Insufficient sample was available to study the elemental composition of preparation 1.

Preparation 1 bound greater than 60% of the phosphate across the pH range 3-7. Preparation 2 reproducibly bound greater than 30% of the phosphate across the pH range 3-8 (Table 7. FIG. 7) This was pH dependent with a mean of 27% less phosphate being bound at pH 8 than pH 3.

TABLE 7

Phosphate binding for preparations with the predicted 2:1 $Mg^{2+}:Fe^{3+}$ ratio

| | percentage phosphate binding at | | | |
|---|---|---|---|---|
| | pH 3 | pH 5 | pH 7 | pH 8 |
| Prep 1 | 77 | 75 | 65 | — |
| Prep 2 (exp. 1) | 50 | 48 | 41 | 37 |
| Prep 2 (exp. 2) | 42 | 39 | 38 | 30 |

2.3 A Magnesium, Calcium and Ferric Iron Containing Preparation (i) A Predicted $Ca^{2+}:Mg^{2+}:Fe^{3+}$ Ratio of 3:3:2

One calcium magnesium ferric iron preparation with a predicted 3:3:2 ratio was synthesised. When this was hydrolysed, elemental analysis showed the measured calcium to magnesium to ferric iron ratio to be 2.9:2.3:2.

This compound bound greater than 45% of the phosphate in solution across the pH range 3-8 (FIG. 7). Two separate experiments showed that the phosphate binding was reproducible (Table 8). Binding was pH dependent with a mean of 36% less phosphate precipitated at pH 8 than pH 3.

TABLE 8

Phosphate binding for preparation with a predicted 3:3:2 $Ca^{2+}:Mg^{2+}:Fe^{3+}$ ratio

| | Percentage phosphate binding at | | | |
|---|---|---|---|---|
| | pH 3 | pH 5 | pH 7 | pH 8 |
| exp. 1 | 80 | 77 | 65 | 54 |
| exp. 2 | 80 | 78 | 64 | 48 |

R2.4 Phosphate Binding by Conventional Compounds

The compounds aluminium hydroxide, magnesium hydroxide and calcium carbonate were also tested for their ability to bind phosphate. The method was as previously described in M4.

All compounds were tested twice and showed reproducible phosphate binding across the pH range studied and the results are shown in FIG. 8 and Table 9 below. In FIG. 8, values plotted are the mean of two separate experiments for each compound.

As can be seen, phosphate binding was pH dependent with a mean 2.4 fold increase in binding by $Al(OH)_3$ at pH 3 compared to pH 8. $Mg(OH)_2$ bound a mean 3.7 times more phosphate at pH 3 than pH 8. $CaCO_3$ bound a mean of 5.9 times more phosphate at pH 3 than pH 8.

TABLE 9

Phosphate binding by $Al(OH)_3 \cdot Mg(OH)_2$ and $CaCO_3$

| | Percentage phosphate binding at | | | |
|---|---|---|---|---|
| | pH 3 | pH 5 | pH 7 | pH 8 |
| $Al(OH)_3$ | 20 | 19 | 18 | 9 |
| $Al(OH)_3$ | 30 | 25 | 23 | 12 |
| $Mg(OH)_2$ | 81 | 82 | 54 | 17 |
| $Mg(OH)_2$ | 87 | 80 | 58 | 28 |
| $CaCO_3$ | 69 | 63 | 30 | 8 |
| $CaCO_3$ | 72 | 70 | 43 | 16 |

EXAMPLE 4

Calcium Sulphate as Phosphate Binder

The following compounds were tested as phosphate binders:
1. Anhydrous calcium sulphate treated with sodium hydroxide
2. Anhydrous calcium sulphate
3. $CaSO_4, 2H_2O$.
4. Ferrous/ferric co-precipitate
5. Ferric precipitate 1. Anhydrous Calcium Sulphate Treated with Sodium Hydroxide This was prepared by mixing anhydrous calcium sulphate ($CaSO_4$) (0.1 moles), with sodium hydroxide (NaOH) (0.2 moles) in 100 ml de-ionised water for 30 minutes at room temperature. The mixture was centrifuged for 2 min at 3000 rpm and the supernatant discarded. The residue was washed by mixing with 100 ml water for 5 minutes followed by centrifugation for 2 min at 3000 rpm. The supernatant was discarded and the washing procedure repeated a further three times. The resultant solid was heated to constant dry weight at 60° C.

2. Anhydrous Calcium Sulphate

A commercially available dry anhydrous calcium sulphate powder was used.

3. Calcium Sulphate Dehydrate

A commercially available calcium sulphate dihydrate powder was used.

4. Ferrous/Ferric Co-Precipitate

This was prepared by co-precipitating ferrous sulphate $FeSO_4$ and ferric sulphate $Fe_2(SO_4)_3$ with sodium hydroxide to obtain a hydrated iron oxide compound. The predicted $Fe^{2+}:Fe^{3+}$ ratio was 3:1.

5. Ferric Precipitate

This was prepared by mixing ferric sulphate ($Fe_2(SO_4)_3$) (0.1 moles), with sodium hydroxide (NaOH)(0.3 moles) in 100 ml de-ionised water for 30 minutes at room temperature.

The mixture was centrifuged for 5 min at 3000 rpm and the supernatant discarded.

The precipitate was washed by mixing with 100 ml water for 5 minutes followed by centrifugation for 5 min at 3000 rpm. The supernatant was discarded and the washing procedure repeated a further 3 times.

The precipitate was heated to constant dry weight at 60° C.

Phosphate Binding

The phosphate binding capacity of each of the above materials was measured as described above in Example 3, using one gram of each compound in 25 ml phosphate solution 40 mmol $l^{-1}$, pH 3-8.

The results are shown in Table 10 below.

TABLE 10

Phosphate binding over the pH range 3-8 by alkali treated calcium sulphate, anhydrous and hydrated calcium sulphates and an $Fe^{2+}:Fe^{3+}$ compound with a predicted 3:1 ratio and an $Fe^{3+}$ compound

| Compound | Percentage phosphate bound at | | | |
|---|---|---|---|---|
| | pH 3 | pH 5 | pH 7 | pH 8 |
| Treated $CaSO_4$ | 100 | 100 | 100 | 100 |
| Anhydrous $CaSO_4$ | 2 | 7 | 47 | 55 |
| $CaSO_4 \cdot 2H_2O$ | 0 | 0 | 57 | 89 |
| $Fe^{2+}:Fe^{3+}$ 3:1 | 26 | 18 | 33 | — |
| $Fe^{3+}$ | 56 | 59 | 56 | 41 |

From the above, it can be seen firstly that mixed metal compounds preferably containing each of a ferric cations and at least one of magnesium, calcium, lanthanum and cerium cation, and at least one of hydroxyl and carbonate anions and optionally at least one of sulphate, chloride and oxide have excellent phosphate binding capacity at a buffer pH relevant to physiological conditions in the gastrointestinal tract.

In particular, they show excellent phosphate binding capacity over a pH range of from 2-8, especially 3-7, and are therefore able to bind phosphate both in the stomach region (upper tract) where the pH would normally be about 3-4, up to 7, possibly depending upon the pH of the binder itself, and also in the lower tract, for example in the duodenum or jejunum, where the pH is likely to be ≥7.

In view of this high binding capacity, lower dosages are possible.

Moreover, for the same weight of phosphate binding compound a mixed calcium/ferric compound contains less ferric ion than the corresponding compound containing iron alone. This allows a small in vivo dosage of iron for at least the same phosphate binding capacity, thus raising the likely tolerance of a patient to the dosage given.

The phosphate binding capacity of the mixed magnesium/ferric compound, is also remarkably less pH dependent as compared with magnesium hydroxide. Moreover, the magnesium tends to be stabilised, leading to a lower expected release thereof when administered in vivo with expected reduced side effects such as hypermagnesaemia. Likewise, the iron tends to be stabilised, leading to a lower expected release thereof in vivo, with an expected reduction in the free radical formation in vivo often encountered with $Fe^{3+}$ ions, so leading to less damage of membrane tissue.

It is also found, particularly surprisingly, that the above also applies to calcium sulphate after treatment thereof with an alkali solution.

EXAMPLE 5

Mixed Metal Hydroxy Carbonate as Phosphate Binders—In Vivo Study in Rats

Materials and Methods

The following chemicals unless otherwise stated were GPR grade from BDH/Merck (Poole, UK): $CaSO_4$, $Fe_2(SO_4)_3 \cdot xH_2O$ (technical grade), $MgSO_4$, $CaCO_3$, NaOH, 70% Nitric acid (redistilled, 99.99% purity). $Al(OH)_3$ and $Mg(OH)_2$ were obtained from Sigma (Poole UK). CT100 was obtained from Crosfield Ltd (Warrington, UK).

Phosphate binders were incorporated into the standard rat diet rat/mouse maintenance No1 food obtained from Lilico (Betchworth, Surrey UK).

Production of the CT Compounds

CTFeCa and CTFeMg were mixed metal hydrotalcites, having a predicted ratio of $Mg^{2+}$ or $Ca^{2+}:Fe^{3+}$ of 3:1, produced in the laboratory following a standard laboratory procedure for mixed metal hydroxyl carbonate preparations as described in Example 3 (M2). This metal$^{2+}$ sulphate, 6 moles, and metal$^{3+}$ sulphate, 2 moles, were dissolved in 4 liters de-ionised $H_2O$. In a separate flask, 16 moles NaOH and 5 moles $Na_2CO_3$ were dissolved in 4 liters de-ionised $H_2O$. The two solutions were pumped using peristaltic pumps into a flask with an overflow at ~2 liters, the rate of addition of the solutions was such that when mixed, the resulting suspension had a pH of 10.0-10.5. After discarding the first liter, by which time a steady state had been established, 3-4 liters of overflowing slurry was collected. This was vacuum filtered using a Buchner flask and washed with 1 liter de-ionised water three times. To allow incorporation into rat food, the wet "cake" compound was dried to constant dry weight at 50° C. and ground with a mortar and pestle.

In Vivo Studies in the Rat

Twenty eight rats (Sprague-Dawley strain), weight range 275-307 grams were divided into seven groups, each consisting of four animals (in Tables 11-14, n=4). The phosphate binders were incorporated into the rat food at a concentration of 1% (w/w). Each group of rats was fed a single diet ad libitum for seven days and had unlimited access to de-ionised water. Animals were then weighed and transferred to metabowls for 24 hours where they received 18 grams of the control diet and unlimited access to water. Total 24 hour urine and faecal output was collected during this time. At the end of the treatment periods, animals were reweighed and a blood sample was obtained via the carotid artery following anaesthetisation with sodium pentobarbitone (Sagatal) 0.1 ml/100 g body weight of a 60 mg/ml solution.

Preparation of Faeces and Urine

Due to the design of the metabowls, the rat faeces were unavoidably contaminated with control food from the diet and there was also slight contamination of the urine. Prior to analysis, food was therefore separated from the urine by 5 minutes centrifugation at 1500 rpm. The food pellet was discarded. Contaminating particulate food was removed from the faeces using forceps and the stool sample weighed.

Total faecal samples from each animal were mixed to ensure a homogeneity and duplicate one gram aliquots weighed. The percentage hydration of the stool was calculated following freeze drying to constant weight.

For measurement of total faecal phosphate and metal ion content, freeze dried faeces was ground with a mortar and pestle and 200 mg hydrolysed by heating to 70° C. for 4 hours with 7 ml concentrated nitric acid in polypropylene test tubes. The faecal digests were diluted to 50 ml with de-ionised water in acid washed 125 ml Nalgene containers.

For measurement of soluble faecal phosphate and metal ion content, a 1.5 gram aliquot of stool was suspended in 15 ml deionised water. Following homogenisation and centrifugation at 3000 rpm for 45 minutes, the supernatant was filtered through glass wool to remove contaminating particulate matter and stored at −20° C.

Analytical Methods

Phosphate, iron and calcium were determined in the faecal digest solutions, urine and serum using standard Boehringher Mannheim chemistry on a Hitachi 911 autoanalyser. Magnesium was measured in the faecal digest solutions, urine and serum using flame photometry atomic absorption spectrometry. Urine and serum aluminium were measured using graphite furnace atomic absorption spectrometry.

Differences between treatment groups was assessed using Students t-test with p<0.05 being considered significant.

Procedure

All animals were weighed daily during the course of the study to ensure that food modified by the addition of phosphate binding compounds did not affect weight gain. During the seven day equilibration period, groups of animals treated with CTFeCa, CTFeMg, $Mg(OH)_2$, $CaCO_3$ or CT100 showed a range of mean weight gains from 38-53 grams. Rats treated with $Al(OH)_3$ showed a mean weight gain of 3 grams. The control group demonstrated a reluctance to eat the standard RMI diet (without addition of phosphate binders). After four days, it was necessary to switch them to a control diet (Lilico). These control animals showed a mean weight loss of 17.5 grams during this seven day period. Soluble phosphate was measured in the Lilico diet and found to be 6.8 $\mu mol\ g^{-1}$, similar to that of the RMI diet without addition of binders, 7.5 $\mu mol\ g^{-1}$.

Following feeding with the modified diets for 7 days, animals were transferred to metabowls for collection of total 24 hour faecal and urine excretion. To ensure that any contamination of faeces and urine by food was similar for the different groups, each animal was given a restricted 18 grams of control diet (Lilico). During this period, control animals gained a mean of 3 grams in weight. Other animal groups showed a mean weight loss of 2-22 grams.

Results

Measurement of Urine and Faecal Phosphate Excretion.

Reduced phosphate absorption achieved when a dosage of the inorganic compound is ingested with food is manifested by a low urine phosphate content, a high total faecal phosphate content and a low ratio of soluble faecal phosphate content:total faecal phosphate content (Table 11).

Differences in urinary phosphate concentration between animals groups could be explained by significant differences in urine volume. Renal phosphate excretion was therefore expressed as total ($\mu mol$) per 24 hours. Animals treated with $Al(OH)_3$ and $CaCO_3$ excreted 1259±279 $\mu mol$ phosphate and 857±25 $\mu mol$ phosphate (mean±SEM) respectively (FIG. 9, Table 11). These values were significantly higher than from rats treated with CTFeCa, CTMgFe, CT100 or $Mg(OH)_2$ mean 71±44 $\mu mol$, 13±4 $\mu mol$, 26±11 $\mu mol$ and 65±53 $\mu mol$ phosphate respectively. No group treated with phosphate binding compounds showed a significant difference in urinary phosphate excretion compared to the controls, mean 466±188 $\mu mol$. This may be explained by a lower food intake by the control animals, demonstrated by their mean weight loss over the course of the study.

To indicate whether phosphate binders were precipitating phosphate in the rat gastrointestinal tract, total stool phosphate (bound and soluble) and soluble stool phosphate {unbound) were measured. To control for variations in faecal output and faecal hydration between groups, faecal phosphate was expressed as $\mu mol$ phosphate $g^{-1}$ dry weight faeces. Total (soluble and insoluble) phosphate $g^{-1}$ dry weight faeces did not differ significantly between any of the treatment groups. Faeces from animals treated with CTFeCa contained significantly less soluble phosphate than the controls or the animals treated with $CaCO_3$ (Table 11). Mean soluble phosphate $g^{-1}$ dry weight faeces as a percentage of mean total phosphate $g^{-1}$ dry weight faeces was 41.9%, 44.8%, 55.9%, 60.7% and 45.0% for animals treated with CTFeCa, $Mg(OH)_2$, $Al(OH)_3$, CT100 and CTFeMg respectively. Soluble phosphate consisted of 79.0% of the total in the control group and 85.5% of the total in the $CaCO_3$ treated group (FIG. 10). These results demonstrate the effectiveness of the CT compounds as binders, decreasing the available phosphate compared to controls and $CaCO_3$ treated animals.

TABLE 11

Mean (±1SEM) urine and faecal phosphate excretion for control rats and those treated with phosphate binding compounds.

| | Control | $Al(OH)_3$ | $CaCO_3$ | CTFeCa | $Mg(OH)_2$ | CT100 | CTFeMg |
|---|---|---|---|---|---|---|---|
| Urine phosphate $\mu mol$ (n = 4) | 466 ± 188* | 1259 ± 279 | 857 ± 25 | 72 ± 44* | 65 ± 53* | 26 ± 11* | 13 ± 4* |
| Total faecal phosphate $\mu mol\ g^{-1}$ dry weight faeces (n = 4) | 150 ± 32 | 188 ± 26 | 213 ± 16 | 181 ± 12 | 183 ± 17 | 181 ± 40 | 206 ± 34 |
| Soluble faecal phosphate $\mu mol\ g^{-1}$ dry weight faeces (n = 4) | 120 ± 6 | 96 ± 9 | 181 ± 9Δ | 73 ± 12Φ | 87 ± 14 | 100 ± 15 | 128 ± 8 |

*p < 0.05 compared to $Al(OH)_3$ and $CaCO_3$ treated animals.
Δp < 0.05 compared to all groups
Φp < 0.05 compared to Control and CTFeMg treated animals.

Measurement of Metal Extraction and Retention

Urine Aluminium Excretion, Serum Aluminium Concentration

Urine and serum aluminum concentrations were measured using graphite furnace atomic absorption spectroscopy. For the animals taking $Al(OH)_3$ or CT100, mean serum aluminum concentrations were not significantly higher than serum aluminum from control animals (Table 12). Surprisingly, animals treated with CTFeCa and CTFeMg showed the highest mean serum aluminum concentrations, both significantly higher than animals treated with $Mg(OH)_2$, $Al(OH)_3$, $CaCO_3$ or controls.

Due to significant differences in total urine volume between different animal groups, aluminium was expressed as $\mu g$ excreted. For animals treated with $Al(OH)_3$, mean urinary $Al^{3+}$ excretion was at least 2 fold higher than animals treated with any other phosphate binder (Table 12). The animals treated without binders (control diet) surprisingly excreted more aluminium than the animals treated with $Al(OH)_3$.

Measurement of Urine Calcium Excretion, Serum Calcium Concentration

Total urinary calcium excretion from $CaCO_3$ treated animals was not significantly different to controls or animals treated with CTFeCa or $Al(OH)_3$. $CaCO_3$ treated animals excreted significantly more calcium than animals treated with $MgOH_2$, CT100 or CTFeMg (Table 13).

Control animals and those treated with $Al(OH)_3$ had significantly higher serum calcium concentrations than animals supplied with any other treatment (Table 13). Rats treated with $CaCO_3$ had significantly higher serum calcium than those treated with $Mg(OH)_2$, CT100 or CTFeCa.

Measurement of Urine Magnesium Excretion

Urinary magnesium excretion following treatment with the compounds CT100 and CTFeMg was higher although not significantly so compared to the control animals (Table 14). Following $Mg(OH)_2$ administration, urine magnesium excretion was significantly higher than the control group or animals treated with any other binder.

Measurement of Urinary and Serum Iron Concentration

In all urine samples from all treatment groups, iron concentration was at the limit of detection of the method employed (>1 $\mu mol\ 1^{-1}$).

Release of iron from the phosphate binders was of concern and so serum iron concentrations were measured in all animals. There was however no significant difference in serum iron concentration between any of the treatment groups (Table 14).

TABLE 12

Mean (±1SEM) urine aluminium excretion, mean (±1SEM) serum aluminium concentration for control rats and those treated with phosphate binding compounds.

| Treatment | Urine aluminium μg (all n = 4) | Serum aluminium μmol $1^{-1}$ |
|---|---|---|
| Control | 1.23 ± 0.05α | 0.45 ± 0.04 |
| Al(OH)$_3$ | 1.07 ± 0.38β | 0.38 ± 0.03 |
| CaCO$_3$ | 0.50 ± 0.21 | 0.33 ± 0.05 |
| CTFeCa | 0.18 ± 0.12 | 0.66 ± 0.07* |
| Mg(OH)$_2$ | 0.17 ± 0.07 | 0.35 ± 0.08 |
| CT100 | 026 ± 0.09 | 0.65 ± 0.24 |
| CTFeMg | 0.31 ± 0.09 | 0.65 ± 0.05* |

*p < 0.05 compared to Mg(OH)$_2$, Al(OH)$_3$, CaCO$_3$ and control treated animals
αp < 0.05 compared to Mg(OH)$_2$, Al(OH)$_3$, CaCO$_3$, CTFeMg, CT100 and CTFeCa treated animals
βp < 0.05 compared to Mg(OH)$_2$, Al(OH)$_3$, CTFeMg, CT100 and CTFeCa treated animals

TABLE 13

Mean (±1SEM) urine calcium excretion, mean (± 1SEM) serum calcium concentration for control rats and those treated with phosphate binding compounds.

| Treatment | Urine calcium μmol | Serum calcium mmol $1^{-1}$ |
|---|---|---|
| Control | 317 ± 94 | 3.29 ± 0.16 (n = 3)α |
| Al(OH)$_3$ | 539 ± 242 | 3.27 ± 0.07 (n = 3)α |
| CaCO$_3$ | 472 ± 17* | 2.93 ± 0.09 (n = 4)β |
| CTFeCa | 333 ± 80 | 2.48 ± 0.10 (n = 4) |
| Mg(OH)$_2$ | 360 ± 62 | 2.58 ± 0.05 (n = 3) |
| CT100 | 314 ± 20 | 2.54 ± 0.07 (n = 4) |
| CTFeMg | 300 ± 34 | 2.69 ± 0.07 (n = 4) |

*p > 0.05 compared to CT100, Mg(OH)$_2$ and CTFeMg treated animals
αp > 0.05 compared to CTFeCa, Mg(OH)$_2$, CT100 and CTFeMg treated animals
βp < 0.05 compared to Mg(OH)$_2$, CTl00 or CTFeCa treated animals

TABLE 14

Mean (±1SEM) urine magnesium excretion, mean (±1SEM) serum iron concentration for control rats and those treated with phosphate binding compounds.

| Treatment | Urine calcium μmol (all n = 4) | Serum iron mmol $1^{-1}$ |
|---|---|---|
| Control | 6.3 ± 1.8 | 37.8 ± 11.2 (n = 3) |
| Al(OH)$_3$ | 9.7 ± 0.6 | 38.5 ± 15.9 (n = 3) |
| CaCO$_3$ | 8.7 ± 1.8 | 41.9 ± 10.8 (n = 4) |
| CTFeCa | 5.9 ± 1.2 | 23.9 ± 5.1 (n = 4) |
| Mg(OH)$_2$ | 17.3 ± 2.3* | 29.4 ± 7.9 (n = 3) |
| CT100 | 9.2 ± 0.6 | 39.5 ± 10.8 (n = 4) |
| CTFeMg | 11.4 ± 0.7 | 48.5 ± 12.5 (n = 3) |

*p < 0.05 compared to all groups

Discussion of Results

As phosphate binders are administered in relatively large doses over long periods of time, metal ion release, absorption and toxicity is of prime concern. Serum aluminium concentration in $Al(OH)_3$ or CT100 treated animals was not significantly higher than animals treated with any other binder. This is in agreement with a human study which reported no increase in serum aluminum, measured up to seven hours after administration of 6 grams hydrotalcite (CT100) [Van der Voet and de Wolff, Clin. Tox. (1986-87), 24, 545-553]. As only ~0.1% of an ingested aluminum dose is absorbed [Powell and Thompson, Proc. Nutr. Soc., (1993) 52, 241-253], changes in the large serum volume are at the limits of accurate measurement.

We therefore measured urinary aluminium excretion as an indicator of intestinal uptake. Animals treated with $Al(OH)_3$ excreted at least 2 fold more aluminium than those treated with any other binder and four fold more than CT100 treated rats. Conclusions as to the relative benefits of CT100 in terms of aluminium release are however limited due to the high urinary excretion from the controls.

Release and absorption of iron from the CTFeCa and CTFeMg binders was of concern as body iron content is regulated by absorption from the gastrointestinal tract [McCance and Widdowson, Lancet, (1937) 2, 680-684]. There is no physiological route by which it can be excreted and daily losses are low, urine<0.1 mg, skin losses 0.2-0.3 mg and faeces 0.6 mg [Bothwell, Nutr. Ron. (1995), 53, 237-245]. Animals treated with CTFeCa or CTFeMg did not show an increase in serum iron compared to animals treated with non iron containing binders or controls and as expected, urine iron excretion was at the limit of detection in all groups.

Compared to animals treated with any other binder, there was at least a 66% and 113% increase in soluble faecal iron in CTFeCa or CTFeMg treated animals respectively. Whether this was absorbable was beyond the scope of this study as complex factors including diet and iron store size influence non-haem iron uptake [Bothwell, Supra: Cook, Am. J. Clin. Nutr. (1990), 51, 301-308]. However, as a number of haemodialysis patients are anaemic, an increased iron load may be beneficial [Remussi and Rossi, in The Kidney (Ed. Brenner, B M), W. B. Saunders, Philadelphia, (1996), Chapter 50, pp 2170-2186].

Different magnesium salts have been shown to have efficacy as phosphate binders. Magnesium carbonate has been shown to be an efficient binder [O'Donovan et. al., Lancet, (1986), 51, 880-881] while magnesium hydroxide has been shown to be ineffective or poorly tolerated [Guillot et al., Nephron, (1982), 30, 114-117; Oe et al., Colin. Nephrol, (1987), 28, 180-185]. Care must be taken though to avoid over administration due to the laxative effects of magnesium. In this study none of the animal groups treated with $Mg(OH)_2$, CT100 or CTFeMg showed an increase in faecal hydration compared to the controls suggesting a dose that was well tolerated by the animals. Neither urine nor serum magnesium were elevated in CTFeMg or CT100 treated animals, suggesting that Mg absorption from these compounds was low.

In summary, CT100, CTFeMg and CTFeCa are all high capacity phosphate binders when administered in vivo to rats at low doses. This study indicates they are likely to have limited toxicity although long time course studies are required to evaluate iron, aluminium and magnesium absorption. These compounds may present effective alternatives to the currently prescribed phosphate binders.

The invention claimed is:

1. A pharmaceutical composition comprising a pharmaceutically acceptable phosphate-binding, mixed metal compound, wherein said compound is free from aluminum and contains iron (III), at least one additional metal M selected from the group consisting of magnesium, calcium, lanthanum and cerium, and a metal sulphate, and wherein the composition is effective for binding phosphate in animal.

2. A pharmaceutical composition as claimed in claim 1 in which the ratio M:Fe for the compound is at least 1.7:1.

3. A pharmaceutical composition as claimed in claim 1 in which the ratio M:Fe for the compound is up to 5:1.

4. A pharmaceutical composition as claimed in claim 1 in which the at least one additional metal is calcium.

5. A pharmaceutical composition as claimed in claim 1 in which the at least one additional metal is magnesium.

6. A pharmaceutical composition as claimed in claim 1 in which the compound additionally contains at least one of a chloride and oxide.

7. A pharmaceutical composition as claimed in claim 1 in which said compound has a phosphate binding capacity of at least 30% by weight, as measured by any of the following methods (1) or (2), over a pH range of 3 to 7:
 (1) adding 1 gram of said mixed metal compound to 25mL of 40 mmol I-1 sodium
 phosphate buffer solution, homogenizing and gently agitating at room temperature
 temperature for 30 minutes, centrifuging at 3000 rpm for 5 minutes, filtering
 through 0.22μm millipore filter and measuring the soluble phosphate in the
 supernatant thus produced;
 (2) adding 1 gram of said mixed metal compound to 25 mL of 20 mmol I-1 sodium
 phosphate buffer solution, homogenizing and gently agitating at room temperature
 temperature for 30 minutes, centrifuging at 3000 rpm for 5 minutes, filtering through 0.22 μm millipore filter and measuring the soluble phosphate in the
 supernatant thus produced.

8. A pharmaceutical composition as claimed in claim 7 in which said compound has a phosphate binding capacity of at least 30% by weight of the total weight of phosphate present as measured by said method (1) or by said method (2) over a pH range of 2 to 8.

9. A pharmaceutical composition as claimed in claim 1 in which said metal compound contains hydroxyl and/or carbonate ions.

10. A pharmaceutical composition as claimed in claim 1 in which said compound has a hydrotalcite type structure.

11. The pharmaceutical composition according to claim 1, wherein the mixed metal compound is unaged.

12. The pharmaceutical composition according to claim 1, wherein the pharmaceutical composition is in the form of a unit dose.

13. A method for binding phosphate in an animal in need thereof, which comprises administering to said animal, a therapeutically effective amount of a pharmaceutically acceptable phosphate-binding, inorganic mixed metal compound, wherein said compound is free of aluminum and contains iron (III) and at least one additional metal M selected from the group consisting of magnesium, calcium, lanthanum and cerium.

14. A method as claimed in claim 13 in which the ratio M:Fe for the compound is at least 1.7:1.

15. A method as claimed in claim 13 in which the ratio of M:Fe for the compound is up to 5:1.

16. A method as claimed in claim 13 in which the at least one additional metal is calcium.

17. A method as claimed in claim 13 in which the at least one additional metal is magnesium.

18. A method as claimed in claim 13 in which the compound additionally contains at least one of sulphate, chloride and oxide.

19. A method as claimed in claim 13 in which said compound has a phosphate binding capacity of at least 30% by weight, as measured by any of the following methods (1) or (2), over a pH range of 3 to 7:
 (1) adding 1 gram of said mixed metal compound to 25 mL of 40 mmol I-1 sodium
 phosphate buffer solution, homogenizing and gently agitating at room temperature
 temperature for 30 minutes, centrifuging at 3000 rpm for 5 minutes, filtering through 0.22 μm millipore filter and measuring the soluble phosphate in the supernatant thus produced;
 (2) adding 1 gram of said mixed metal compound to 25 mL of 20 mmol I-1 sodium phosphate buffer solution, homogenizing and gently agitating at room temperature temperature for 30 minutes, centrifuging at 3000 rpm for 5 minutes, filtering through 0.22 μm millipore filter and measuring the soluble phosphate in the supernatant thus produced.

20. A method as claimed in claim 19 in which said compound has a phosphate binding capacity of at least 30% by weight of the total weight of phosphate present as measured by said method (1) or by said method (2) over a pH range of 2 to 8.

21. A method as claimed in claim 13 in which said metal compound contains hydroxyl and/or carbonate ions.

22. A method as claimed in claim 13 in which said compound has a hydrotalcite type structure.

* * * * *